United States Patent
Smith et al.

(10) Patent No.: US 10,288,408 B2
(45) Date of Patent: May 14, 2019

(54) SCANNING WHITE-LIGHT INTERFEROMETRY SYSTEM FOR CHARACTERIZATION OF PATTERNED SEMICONDUCTOR FEATURES

(71) Applicant: Nanometrics Incorporated, Milpitas, CA (US)

(72) Inventors: Nigel P. Smith, Beaverton, OR (US); George Andrew Antonelli, Portland, OR (US)

(73) Assignee: Nanometrics Incorporated, Milpitas, CA (US)

( * ) Notice: Subject to any disclaimer, the term of this patent is extended or adjusted under 35 U.S.C. 154(b) by 0 days.

(21) Appl. No.: 15/388,794

(22) Filed: Dec. 22, 2016

(65) Prior Publication Data
US 2018/0156597 A1    Jun. 7, 2018

Related U.S. Application Data

(60) Provisional application No. 62/429,022, filed on Dec. 1, 2016.

(51) Int. Cl.
*G01B 9/02*    (2006.01)
*G01N 21/45*    (2006.01)
(Continued)

(52) U.S. Cl.
CPC ..... *G01B 9/02043* (2013.01); *G01B 9/02007* (2013.01); *G01B 9/0209* (2013.01);
(Continued)

(58) Field of Classification Search
CPC ............ G01B 9/02057; G01B 9/02083; G01B 9/02088; G01B 9/0209
See application file for complete search history.

(56) References Cited

U.S. PATENT DOCUMENTS 6,963,445 B2    11/2005    Hoover et al.
7,061,623 B2    6/2006    Davidson
(Continued)

FOREIGN PATENT DOCUMENTS

TW    I489083    6/2015
WO    WO 2014/138741 A1    9/2014

OTHER PUBLICATIONS

International Search Report and Written Opinion from PCT/US2017/063685, dated Feb. 5, 2018, 19 pages.

*Primary Examiner* — Jonathan M Hansen
(74) *Attorney, Agent, or Firm* — Silicon Valley Patent Group LLP

(57) ABSTRACT

A white light interferometric metrology device operates in the image plane and objective pupil plane. The interferometric metrology device extracts the electric field with complex parameters and that is a function of azimuth angle, angle of incidence and wavelength from interferometric data obtained from the pupil plane. Characteristics of the sample are determined using the electric field based on an electric field model of the azimuth angle, the angle of incidence and the wavelength that is specific for a zero diffraction order. A center of the pupil in the pupil plane may be determined based on a Fourier transform of the interferometric data at each new measurement and used to convert each pixel from the camera imaging the objective pupil plane into a unique set of angle of incidence and azimuth angle of light incident on the sample.

35 Claims, 18 Drawing Sheets

(51) Int. Cl.
  *G02B 21/00* (2006.01)
  *G01N 21/956* (2006.01)
  *G01N 21/21* (2006.01)
  *H01L 21/66* (2006.01)
  *G02B 21/14* (2006.01)

(52) U.S. Cl.
  CPC ..... *G01B 9/02027* (2013.01); *G01B 9/02035* (2013.01); *G01B 9/02067* (2013.01); *G01B 9/02072* (2013.04); *G01B 9/02084* (2013.01); *G01N 21/45* (2013.01); *G01N 21/956* (2013.01); *G02B 21/0016* (2013.01); *G02B 21/0092* (2013.01); *G01B 2210/56* (2013.01); *G01B 2290/50* (2013.01); *G01B 2290/65* (2013.01); *G01B 2290/70* (2013.01); *G01N 21/21* (2013.01); *G01N 2021/95676* (2013.01); *G02B 21/14* (2013.01); *H01L 22/12* (2013.01)

(56) References Cited

U.S. PATENT DOCUMENTS

| | | | |
|---|---|---|---|
| 7,321,430 B2 | 1/2008 | Deck | |
| 7,324,210 B2 | 1/2008 | De Groot et al. | |
| 7,446,882 B2 | 11/2008 | De Lega et al. | |
| 7,619,746 B2 | 11/2009 | De Lega | |
| 7,808,648 B2 | 10/2010 | Sandstrom | |
| 8,126,677 B2 | 2/2012 | De Groot et al. | |
| 9,243,886 B1 | 1/2016 | Kuznetsov et al. | |
| 2004/0169861 A1* | 9/2004 | Mieher | G01N 21/956 356/400 |
| 2005/0046855 A1 | 3/2005 | Davidson | |
| 2006/0158659 A1 | 7/2006 | Colonna De Lega et al. | |
| 2007/0188768 A1* | 8/2007 | Mansfield | G01B 11/0675 356/504 |
| 2009/0021723 A1 | 1/2009 | De Lega | |
| 2009/0153873 A1* | 6/2009 | Chan | G01N 21/4795 356/495 |
| 2010/0128283 A1 | 5/2010 | Liesener et al. | |
| 2010/0134786 A1 | 6/2010 | De Lega et al. | |
| 2011/0032535 A1* | 2/2011 | Liesener | G03F 7/70633 356/511 |
| 2012/0113431 A1* | 5/2012 | Fukuma | A61B 3/102 356/456 |
| 2014/0111791 A1 | 4/2014 | Manassen et al. | |
| 2014/0233025 A1 | 8/2014 | Den Boef et al. | |
| 2016/0377412 A1* | 12/2016 | Li | G01B 11/0608 356/630 |

\* cited by examiner

SCANNING WHITE-LIGHT INTERFEROMETRY SYSTEM FOR CHARACTERIZATION OF PATTERNED SEMICONDUCTOR FEATURES

CROSS REFERENCE TO RELATED APPLICATIONS

This application claims priority under 35 USC 119 to U.S. Provisional Application No. 62/429,022, entitled "A SCANNING WHITE-LIGHT INTERFEROMETRY SYSTEM FOR CHARACTERIZATION OF PATTERNED SEMICONDUCTOR FEATURES," filed Dec. 1, 2016, which is incorporated herein by reference in its entirety.

FIELD OF THE INVENTION

The present invention is related to optical metrology and in particular to interferometric metrology.

BACKGROUND

Semiconductor and other similar industries, often use optical metrology equipment to provide non-contact evaluation of substrates during processing. One type of optical metrology is scanning white-light interferometry.

A scanning white-light interferometer uses broadband light that is split to produce a probe beam and a reference beam, which when combined produces an interference pattern. A scanning white-light interferometer images conventionally produces a plurality of images of a sample using various path differences between the combined beams. Analysis of the resulting interference fringes with respect to path difference at each pixel of the detector (which corresponds to points on the sample surface provides three dimensional information for surface height profiles of a sample. Thus, the data collected by a scanning white-light interferometry system focused to a given spot size on a given site on a semiconductor wafer contains information describing the local stack of thin films and its pattern. The spot size required for this measurement can in theory be diffraction limited.

SUMMARY

A white light interferometric metrology device operates in the image plane and objective pupil plane. The interferometric metrology device extracts the electric field with complex parameters and that is a function of azimuth angle, angle of incidence and wavelength from interferometric data obtained from the pupil plane. Characteristics of the sample are determined using the electric field based on an electric field model of the azimuth angle, the angle of incidence and the wavelength that is specific for a zero diffraction order. A center of the pupil in the pupil plane may be determined based on a Fourier transform of the interferometric data at each new measurement and used to convert each pixel from the camera imaging the objective pupil plane into a unique set of angle of incidence and azimuth angle of light incident on the sample.

In one aspect, a method of characterizing a sample with a white light interferometer includes obtaining interferometric data from the sample with the white light interferometer, the interferometric data comprising intensity with respect to an optical path difference for each pixel from a camera imaging an objective pupil plane of the white light interferometer when measuring the sample; extracting an electric field with complex parameters from the interferometric data, the electric field being a function of azimuth angle, angle of incidence and wavelength; and determining one or more characteristics of the sample using the electric field based on an electric field model of the azimuth angle, the angle of incidence and the wavelength that is specific for a zero diffraction order.

In one aspect, a white light interferometer capable of characterizing a sample includes a broadband light source that produces an illumination beam of broadband light; a beam splitter that directs the illumination beam toward the sample and directs the illumination beam through an aperture stop at an objective pupil plane, wherein the illumination beam is reflected by the sample to form a reflected beam, the beam splitter directs the reflected beam towards a camera; an interferometric objective lens that receives the illumination beam and focuses the illumination beam on the sample, the interferometric objective lens comprising a reference mirror to form a reference beam, wherein the reflected beam combines with the reference beam to produce interference in the reflected beam based on an optical path difference between the reflected beam and the reference beam; the camera having a plurality of pixels, the camera captures images of the objective pupil plane while the optical path difference is varied to produce interferometric data for the sample, the interferometric data comprising intensity with respect to the optical path difference at each pixel; and at least one processor coupled to receive the interferometric data for the sample, the at least one processor extracts an electric field with complex parameters from the interferometric data, the electric field being a function of azimuth angle, angle of incidence and wavelength, and determines one or more characteristics of the sample using the electric field based on an electric field model of the azimuth angle, the angle of incidence and the wavelength that is specific for a zero diffraction order.

In one aspect, a method of processing white light interferometric data from a sample with a patterned structure includes obtaining interferometric data from the sample with the patterned structure with a white light interferometer, the white light interferometer comprising a pupil in an objective pupil plane and the interferometric data from the sample is obtained from imaging the objective pupil plane, the interferometric data comprising intensity with respect to optical path difference for each pixel from a camera imaging the objective pupil plane when measuring the sample with the patterned structure; performing a Fourier transform of the interferometric data at each pixel; and determining a center of the pupil in the objective pupil plane using the Fourier transform of the interferometric data at each pixel and a spectrum of a light source of the white light interferometer.

In one aspect, a white light interferometer for measuring a sample with a patterned structure includes a broadband light source that produces an illumination beam of broadband light; a beam splitter that directs the illumination beam toward the sample with the patterned structure and directs the illumination beam through a pupil in an objective pupil plane, wherein the illumination beam is reflected by the sample to form a reflected beam, the beam splitter directs the reflected beam towards a camera; an interferometric objective lens that receives the illumination beam and focuses the illumination beam on the sample, the interferometric objective lens comprising a reference mirror to form a reference beam, wherein the reflected beam combines with the reference beam to produce interference in the reflected beam based on an optical path difference between the reflected beam and the reference beam; the camera having a plurality of pixels, the camera captures images of the objective pupil plane while the optical path difference is varied to produce interferometric data for the sample, the interferometric data comprising intensity with respect to the optical path difference at each pixel; and at least one processor coupled to receive the interferometric data for the sample with the patterned structure, the at least one processor performs a Fourier transform of the interferometric data at each pixel, and determines a center of the pupil in the objective pupil plane using the Fourier transform of the interferometric data at each pixel and a spectrum of the broadband light source.

DETAILED DESCRIPTION

A scanning white-light interferometer system of hardware and an analytical method extracts structural information using an optical spot size that is not diffraction limited and may be less than 10 μm. This scanning white-light interferometer relies on operation in the objective pupil plane rather than the image plane. Data for a continuous range of wavelengths defined by the spectrum of the light source and angles of incidence defined by the numerical aperture (NA) of the optical system can be simultaneously measured. The analysis may advantageously use a construction of an electric field model and a system level model of the scanning white-light interferometer hardware, that incorporates hardware based calibrations into the model to be fit to the raw data.

Figure 1:
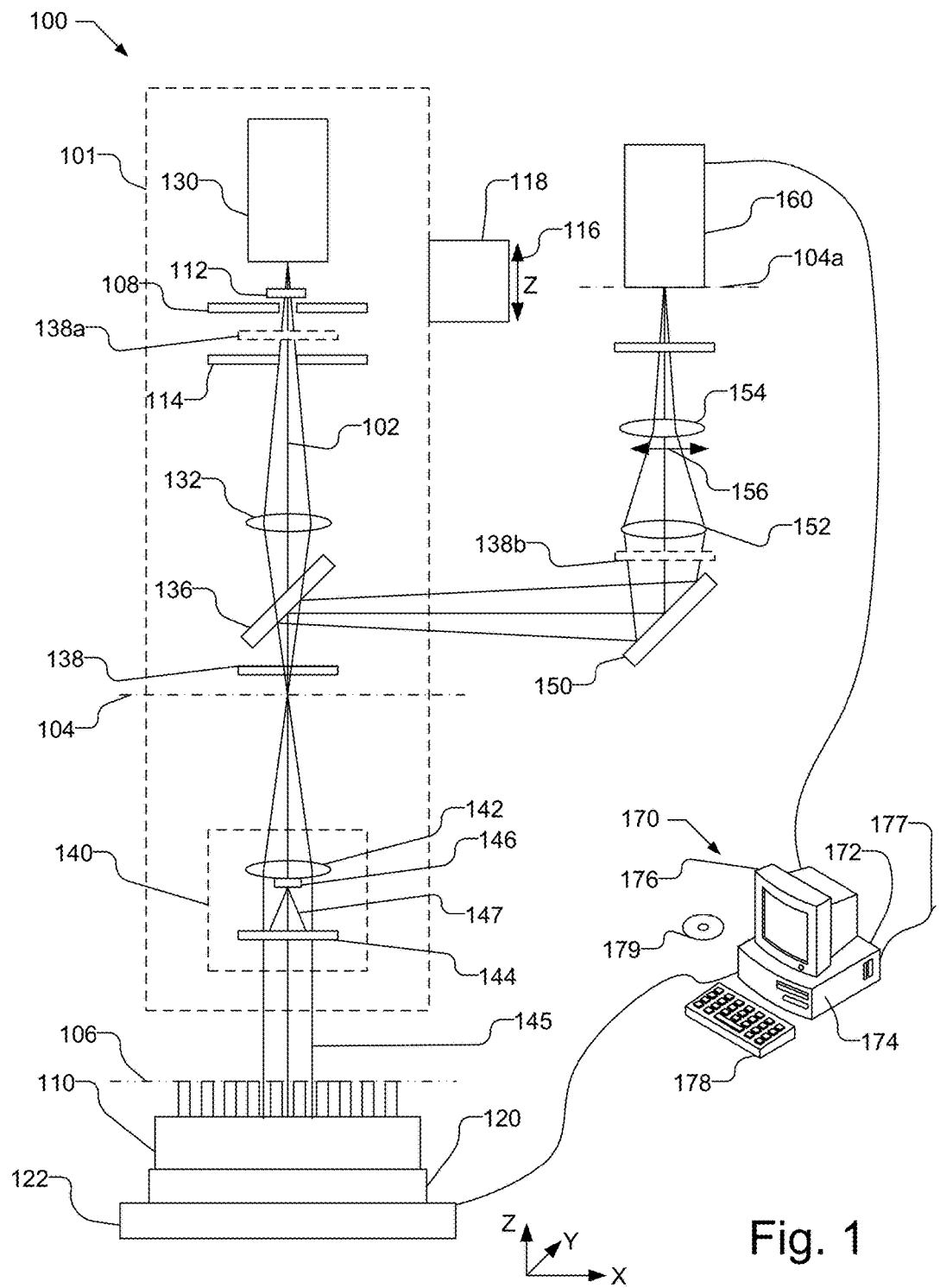
FIGS. 1 and 2 illustrate a schematic view of a scanning white-light interferometer, capable of operating in the objective pupil plane and the image plane to measure one or more physical characteristics of a sample.
Figure 2:
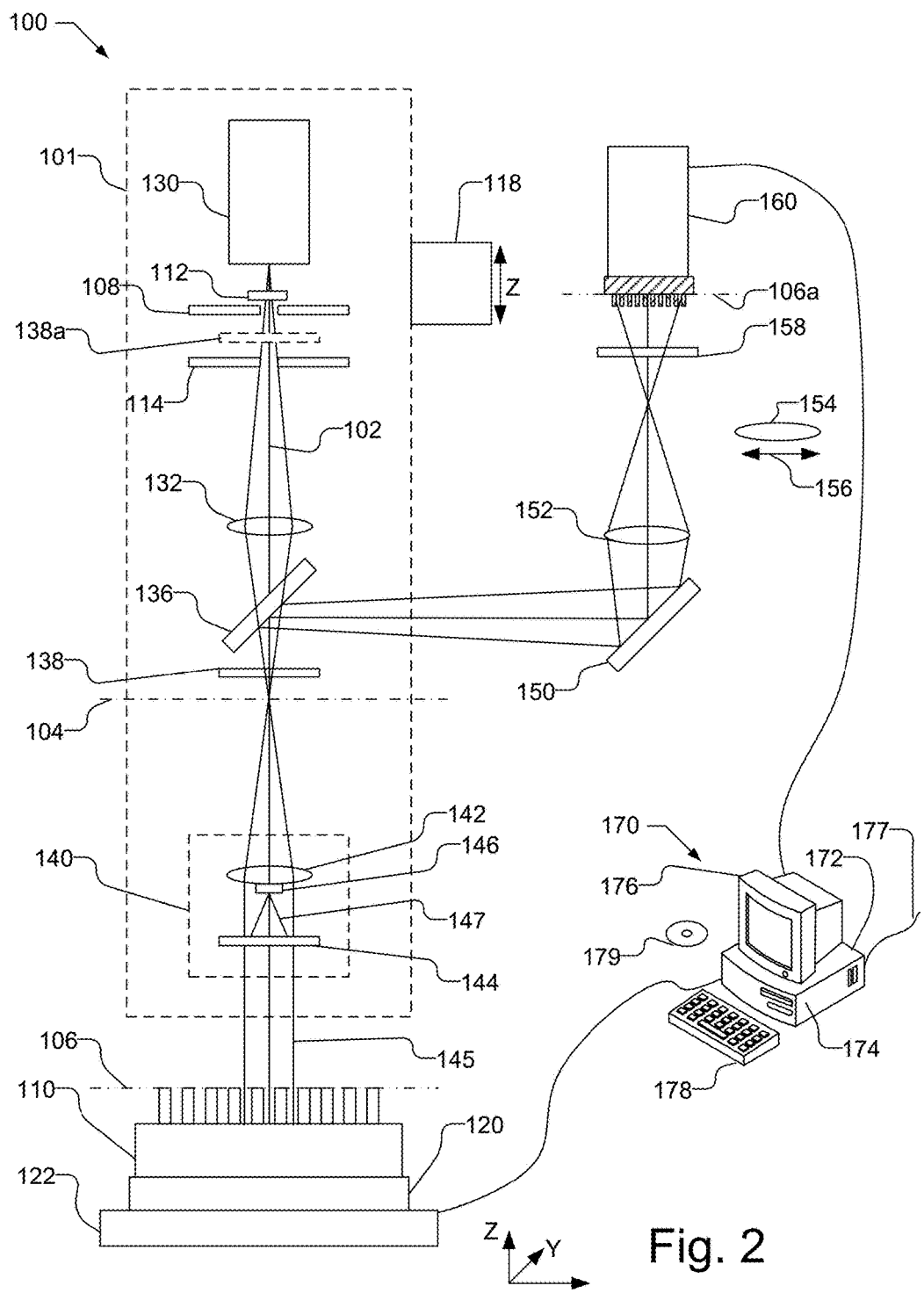

FIGS. 1 and 2 illustrate a schematic view of an optical metrology device 100, which is a scanning white-light interferometer, capable of operating in the objective pupil plane and the image plane to measure one or more physical characteristics of a sample 110. FIG. 1 illustrates the optical metrology device 100 operating in the pupil plane illustrated with dash-dot line 104, while FIG. 2 illustrates the optical metrology device operating in the image plane illustrated with a dash-double-dot line 106 that is aligned with the surface of the sample 120. As illustrated, the metrology device 100 includes chuck 120 mounted on a stage 122. The stage 122 is capable of horizontal motion in either Cartesian (i.e., X and Y) coordinates, or Polar (i.e., R and θ) coordinates or some combination of the two. The stage may also be capable of vertical motion along the Z coordinate.

The optical metrology device 100 is configured for pupil-plane and image-plane detection of through-focus white-light interference signals formed by reflecting light from the surface of the sample 110. The white light interferometer 100 includes a broadband light source 130, an illumination lens 132, and a beam splitter 136. If desired, a second beam splitter facing the opposite direction from beam splitter 136 may be added before or after beam splitter 136 as a mechanism to cancel out any lateral shift caused by beam splitter 136 or to provide a portion of the light to another sensor, e.g., to monitor the light level from the light source 130. The light source 130 generates an illumination beam along optical axis 102. A diffuser 112 may be positioned on the optical axis 102 before the illumination lens 132. The illumination beam passes through an aperture stop 108 followed by a selectable field stop 114. The aperture stop 108 is focused by lens 132 on the objective pupil plane 104 and is directed, e.g., transmitted, by the beam splitter 136 towards an interferometric objective 140. A polarizer 138 may be positioned between the beam splitter 136 and the interferometric objective 140. The polarizer 138 may be, e.g., a linear polarizer, but in some embodiments may be a circular polarizer. The polarizer 138 is illustrated as being positioned before the pupil plane 104, but the polarizer 138 may be positioned after the pupil plane 104. If the pupil plane 104 is within the physical body of the interferometric objective 140, the polarizer 138 may be placed before the pupil plane 104, or incorporated into the body of the objective 140. Incorporating the polarizer 138 into the body of the objective 140, however, requires custom manufacture and renders rotation of the polarizer 138 with respect to the body of the objective 140 more difficult than if the polarizer 138 is separate from the objective 140. If desired, the image of aperture stop 108 formed by lens 132 may be external to the body of the objective 140 and an additional lens may be used to focus the image of aperture stop 108 onto the pupil plane 104, and the polarizer 138 may be placed below the image of the aperture stop 108.

Figure 3:
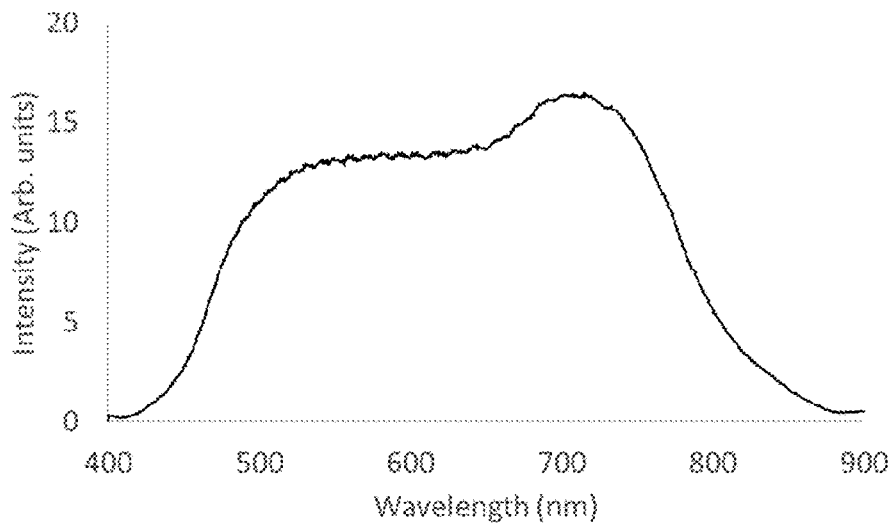
FIG. 3 illustrates a measured spectrum of a Xe arc lamp, which may be used as light source in the scanning white-light interferometer.

The light source 130 may be a single source of broadband light or multiple sources of light having different wavelength ranges that are combined to produce the broadband illumination beam. The light source 130 is preferably incoherent and linearly polarized, and may include an ability to select an array of narrower bands through the use of filters, spectrographs, or other means. The light source 130 may operate at constant intensity with the light level controlled externally by mechanical/optical means, e.g., selectable neutral density, or by electrical means, e.g., camera exposure time. The light source 130 by way of example, and not limitation may be a filament lamp, e.g., W, SiC, etc.; arc lamps, e.g., Xe, D2, etc.; light emitting diodes; plasma lamps that may be excited by microwave, laser, or radio frequency induction consisting of gaseous of solid species including but not limited to Xe, Ar, Ne, Hg, Fe, Mn, etc. and any combination thereof. The emission spectrum of the light source 130 may be in the range of 200 nm to 2 µm, and may be, e.g., in the range of 350 nm to 900 nm. By way of example, FIG. 3 illustrates a measured spectrum of a Xe arc lamp, which may be used as light source 130, as collected by camera 160. As illustrated, the Xe arc lamp source has a useful operating range of 400 to 900 nm, which is determined by a convolution of the spectral properties of the optical elements, camera, and light source.

Light emitted by the light source 130 may be delivered to the imaging optics, e.g., by an appropriately selected optical fiber, liquid light guide, or directly coupled with appropriate interface optics. As optical metrology device 100 images the aperture stop 108 onto the objective pupil plane 104, the intensity and phase of the input beam at the entry to the aperture stop 108 is ideally uniform. The optical metrology device 100 is configured for pupil-plane detection in which the reflectance of a sample will be measured as a function of wavelength, angle of incidence and azimuth angle, by measuring the distribution of emerging light in an image of the pupil plane. Accordingly, if the source distribution is uniform, then the pupil plane image will be much closer to the desired reflectance function than if the source distribution is not uniform. To achieve a uniform light magnitude and phase at the pupil plane 104, the diffuser 112 may be positioned before the aperture stop 108. The diffuser 112 may be a disk diffuser, e.g., with a thickness of 3 mm, or a fused quartz light pipe 10 to 40 mm in length with 7 mm square or circular cross-section with the output surface ground with between 150 and 600 grit. The end of the diffuser 112 is positioned immediately before, and if desired, in contact with, the aperture stop 108 and thus is imaged onto the pupil plane 104 by the lens 132. In practice, however, some structure derived from the light source 130 or its delivery optics, e.g., lens 132 and beam splitter 136, is likely and variation in the magnitude and phase of the illumination may be corrected during analysis. By minimizing variation in the magnitude and phase of the input beam, the need for calibration and maintaining the calibration is reduced. By way of example, for a 12-bit signal with 1024 levels of detection, light source 130 uniformity better than 0.1% is desirable.

The imaging optics image the aperture stop 108 onto the entrance pupil of the final interferometric objective 140 with a selectable field stop 114 appropriately interposed between them. Changing the field stop 114 will change the size of the measurement spot on the sample 110. The desired target range for the spot size, by way of example, is 3 µm to 50 µm. There may be at least two selectable sizes for the field stop 114, e.g., one to yield a spot size in the range of 3-10 µm and another to yield a spot size in the range of 15-30 µm.

Figure 4A:
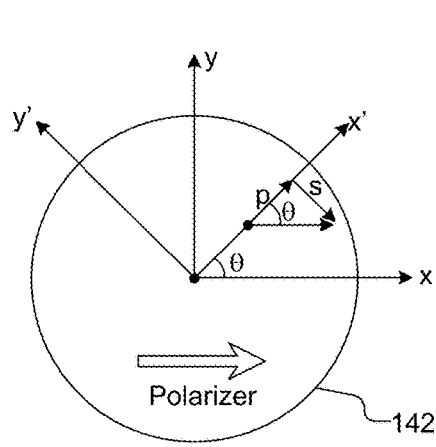
FIGS. 4A and 4B illustrate the geometry of the XY plane above and the XZ plane of a Mirau objective.
Figure 4B:
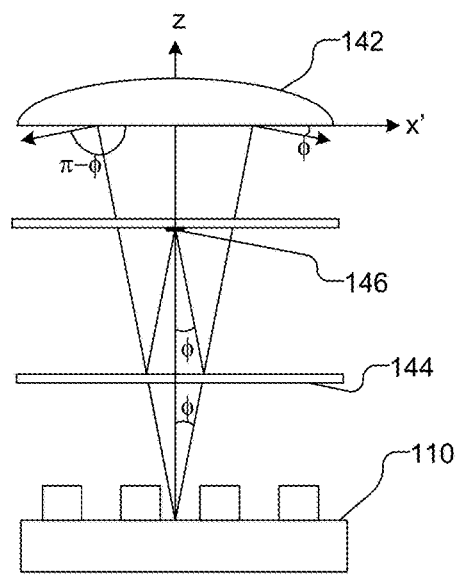

The interferometric objective 140 is configured to split incident light into a probe beam that is reflected from the sample and a reference beam that reflects from a reference surface and is recombined with the light reflected from the sample. The interferometric objective 140 is illustrated, by way of example, as a Mirau objective, including a lens 142, a beam splitter 144, and a reference mirror 146. The separation of the reference mirror 146 and the beam splitter 144 may be, e.g., less than 50 µm. FIG. 4A illustrates the geometry of the XY plane above the Mirau objective 140, where the azimuthal angle is designated θ and FIG. 4B illustrates the geometry of the XZ plane of the Mirau objective 140, where the angle of incidence (AOI) is designated φ. If desired, however, the interferometric objective 140 may be another type of objective, such as a Michelson objective or multiple objectives using a Linnik geometry. Thus, the interferometric objective 140 illustrated in FIG. 1, may be any single or multiple-lens arrangements that provide the necessary wavefront splitting and recombination to allow interference to occur.

The selection of the interferometric objective 140 depends on the interference mechanism of the optical metrology device 100. The interferometric objective 140 is also a central component in the imaging optics. The selected interferometric objective 140 sets the numerical aperture of the system and thus determines the maximum (and the minimum in the case of a Mirau objective) angle of incidence which can be measured. The magnification of the objective plays a central role in setting the field of view and minimum feature size that can be resolved. For the range of spot size between 3 µm to 50 µm, the magnification may be greater than 50×, e.g., 100×, and the numerical aperture should be greater than 0.7, e.g., 0.8.

If desired, the optical metrology device 100 may operate in an immersion mode with water, oil, ethanol, or another liquid to increase the numerical aperture of the objective lens. This mode of operation could also be useful for eliminating undesirable surface features through index matching, i.e., a thick silicon dioxide layer on top of a feature of interest or removal of the scatterometry signal from a silicon dioxide grating.

With an interferometric objective, such as a Mirau objective or a Michelson objective, the system can change the path difference either by moving the objective lens alone or the entire optical assembly 101 relative to the sample 110 by actuator 118, which may be a piezoelectric scanner capable of fine motion in the Z direction. With use of the Linnik geometry, either the reference objective alone, the reference mirror alone, or the entire optical assembly would be moved relative to the sample 110. From an optical perspective, there is no difference between the sample or the entire imaging system moving relative to each other; however, there are practical implications, i.e., the mass of the optical system may limit the selection of the stage which may in turn limit the minimum stage accuracy. Regardless of the method of scanning, there should be a method of bringing the position of the interference fringe pattern to the point of focus on the sample 110. The scanning system should move along a single axis, e.g., Z axis, and must be able to operate in a range of −50 μm to +50 μm about the point of optimal focus, expressed in terms of movement about the focal plane. In some cases, e.g. moving the reference mirror in a Linnik configuration system, the actual movement might be different but it should be understood that this range of motion is the equivalent displacement measured in the focal plane.

FIGS. 1 and 2 illustrate an actuator 118 attached to the optical assembly 101 used to adjust the vertical position of the optical assembly 101, and thus, the interferometric objective 140 along the Z coordinate to vary the path difference between a probe beam 145 incident on the sample 110 and a reference beam 147 incident on the reference mirror 146. It should be understood, however, that with other interferometric objectives, such as a Michelson objective or an interferometric objective using a Linnik geometry, the path difference may be varied by moving a reference mirror in a direction perpendicular to the vertical direction. Nevertheless, for the sake of simplicity, because the path difference between the probe beam 145 and the reference beam 147 is varied in FIG. 1 by adjusting the vertical position of the interferometric objective 140 with respect to the sample, varying the path difference in any type of interferometric objective that may be used in optical metrology device 100 will sometimes be referred to herein as varying the height, varying the z position, or varying the optical path difference.

The illumination lens 132 focuses an image of the aperture stop 108 onto the back focal plane of the interferometric objective 140. Thus, the optical metrology device 100 operates with Kohler illumination. With Kohler illumination, each point in the aperture stop 108 gives rise to a parallel bundle of light that is incident on the sample 110. The angle of incidence of a parallel bundle of light depends only on the distance from the point in the aperture stop 108 from which the bundle of light originates to the optical axis 102. Ideally, the illumination lens 132, the interferometric objective 140 and aperture stop 108, share the same optical axis 102 and the light source 130 is spatially incoherent, so that the light from different points in the aperture stop 108 does not interfere. In practice, the alignment of the illumination lens 132, the interferometric objective 140 and aperture stop 108 with the optical axis 102 will not be ideal, nevertheless, with careful alignment, the optical system may still produce acceptably minimal interference of light from different points in the aperture stop 108 despite non-ideal alignment.

The illumination beam is reflected from the sample 110 and the resulting reflected beam passes back through the interferometric objective 140, polarizer 138, aperture stop 108, and is directed, e.g., reflected, by the beam splitter 136 towards the camera 160. It should be understood that if desired, the beam splitter 136 may reflect the illuminating light from the light source 130 and transmit the light reflected from the sample 110. The reflected beam may be reflected by a mirror 150 and imaged by a lens 152 onto a camera 160. An output polarizer 158 is positioned between the lens 152 and the camera 160. Additionally, an auxiliary lens 154 between lens 152 and a polarizer 158 may be moved into or out of the beam path, as illustrated by the arrows 156.

The auxiliary lens 154, which may be a Bertrand lens, may be moved into the optical axis 102 to image the objective pupil plane 104 onto the camera 160, as illustrated by pupil plane image 104a in FIG. 1. Thus, the optical metrology device 110 is capable of objective pupil plane detection. In pupil plane detection, each point in the image arises from light incident on the sample 110 from only a single direction. Light from all illuminated parts of the sample 110 contribute to the signal at every point in the pupil plane image. The lack of spatial discrimination is appropriate if the sample is unpatterned, e.g., a single flat surface with or without uniform films. When the sample 110 is patterned, as illustrated in FIG. 1, it is desirable to control the size and shape of the illuminated area, referred to as the "probe region." For example, it may be desirable to limit the probe region so that the probe region contains a number of repeating, nominally identical structures. The field stop ("f-stop") 114 is imaged onto the sample and so may be used to control the size and shape of the probe region. The size of the probe region depends on the size of the f-stop 114 and the magnification of the optical system. By way of example, a 400 μm diameter circular f-stop may give rise to an 8 μm diameter circular probe region on the sample 110. Pneumatic actuators or servo mechanisms may be used to move the system from the image to pupil plane and from a large to a small f-stop.

With the auxiliary lens 154 moved out of the optical axis, as illustrated in FIG. 2, the camera receives a magnified image of the image plane 106, illustrated by the cross-hatched sample 110a and image plane 106a at the camera 106. Thus, the optical metrology device 100 is also capable of image plane detection. In image plane detection, every point on the surface of the imaged sample 110 received by the camera 160 has spatial separation from other points on the surface of the sample 110, but light from all parts of the aperture stop 108 contribute to the image at every point.

The optical metrology device 100 has the ability to shift between operation in the image plane and the pupil plane. As illustrated in FIGS. 1 and 2, with the presences of the auxiliary lens 154 in the optical path, the optical metrology device 100 operates in the pupil plane detection mode, and when the auxiliary lens 154 is removed from the optical path, the optical metrology device 100 operates in the image plane detection mode. If desired, however, the optical metrology device 100 may operate in pupil plane detection mode when the auxiliary lens 154 is removed from the optical path and may operate in image plane detection mode when the auxiliary lens 154 inserted into the optical path. In another configuration a beam splitter may be used with two cameras, one configured to provide pupil plane detection and another camera configured to provide image plane detection simultaneously.

The polarizing elements 138 and 158 used in the optical metrology device 100 may be one or a mixture of types including but not limited to thin film, wire grid, prism, cubes, and combinations thereof. Each polarizer 138, 158 may have the ability to rotate either continuously or in increments of 90°. Polarizer 138 is positioned immediately before the interferometric components, e.g., at the input of the interferometric objective 140 and output polarizer 158 is positioned immediately before the camera 160, and thus, polarizes both the illumination beam and the reflected beam. A number of other physical realizations of polarizers may be used with optical metrology device 100. For example, in one instance, in place of polarizer 138, a polarizer 138a, shown with broken lines in FIG. 1, may be is placed between the light source 130 and the beam splitter 136 that separates the detection arm including the lenses 152, 154 and camera 160 from the interferometric objective 140, and another polarizer 138b may be placed in the detection arm. In this instance, light passes through each polarizer 138a and 138b once, and thus, the relative orientations of the two polarizers 138a and 138b should be known. In another instance, polarizer 138 positioned at the input of the interferometric objective 140 may be used along with polarizer 138b in the detection arm, wherein light passes through the first polarizer 138 twice and passes through the second polarizer 138b once. Again, the relative orientations of the two polarizers 138 and 138b should be known. Other possible configurations may be used, for example, if the interferometric objective 140 has a Linnik configuration, possible configurations include a single polarizer at the input to the sample objective, or two polarizers with one at the input to the sample objective and the other at the input to the reference objective, or further combinations thereof.

With the use of multiple polarizers (or multiple passes through a single polarizer 138), it is possible to simultaneously monitor multiple output polarization related signals. For instance, if a polarization set to transmit P polarized light is placed at the output of the light source which is in turn input to an interferometric objective, prior to the detection system a polarizing beam splitter cube 159 could be used to send the P polarized to one camera 160 and the S polarized to the other 160'. In this way, the result of P incident and P resultant or PP signal could be monitored at the same time as the PS. By simply rotating the first polarizer, one would be able to monitor SP and SS.

In addition, if desired, a compensator may be used in addition to the output polarizer 158, e.g., by placing the compensator before the output polarizer 158. The output polarizer 158 may be used to block light that is not aligned with the first polarizer 138. The addition of a compensator would allow one to enhance the signal by adding back light rotated by an element, such as the beamsplitter 136, that is in between the first polarizer 138 and the compensator.

The detection system for the optical metrology device 100 includes camera 160, and may include additional cameras if desired, depending on optical design and the capability of other system components. The detector extent as well as the pixel size for the camera 160 may be selected to be consistent with the size of the image projected onto it by the optical system as a whole as well as the desired resolution. The rate of frame acquisition should be consistent with the scanner motion, so that ideally the scanner moves by the same distance between frames, and by the same distance during the frame capture time. The wavelength sensitivity of the detector of the camera 160 should also be consistent with the light source 130 as well. The bit depth of the camera 160 should have a minimum of 8-bit resolution, but a higher resolution, such as 16-bit, is desirable.

By way of example, the camera 160 may include a CCD detector with 1024×1280 pixels. The camera 160 may be capable of 12-bit operation at up to 30 Hz frame rate. 8-bit operation, hardware binning and region limiting may be used to improve the acquisition rate to 80 Hz with a 256×256 pixel image. Other suitable detectors that may be used include single or multiple one- or two-dimensional arrays of photodetectors such as photodiodes.

It should be understood that the optical system of the optical metrology device 100 may including additional components and/or other imaging configurations, e.g., making pupil-plane detection the default mode of operation and moving an auxiliary lens into the beam path to provide image-plane detection. Alternatively, a beam splitter combined with suitable lenses and cameras may be used for simultaneous pupil-plane and image-plane detection, although there would be a loss of intensity of the received light relative in both modes with respect to optical metrology device 100.

The camera 160 is coupled to a computer 170, such as a workstation, a personal computer, central processing unit or other adequate computer system, or multiple systems. The computer 170 is preferably included in, or is connected to or otherwise associated with optical metrology device 100. The computer 170 may also control the movement of the stage 122, as well as control the operation of the chuck 120. The computer 170 also collects and analyzes the interferometric data obtained from the camera 160 as discussed herein. For example, the computer 170 may analyze the interferometric data to determine one or more physical characteristics of the sample 110 as discussed below. The computer 170 may analyze the interferometric data to determine a center of the pupil plane as discussed below. The computer 170, which includes at least one processor 172 with memory 174, as well as a user interface including e.g., a display 176 and input devices 178. A non-transitory computer-usable storage medium 179 having computer-readable program code embodied may be used by the computer 170 for causing the at least one processor to control the optical metrology device 100 and to perform the functions including the analysis described herein. The data structures and software code for automatically implementing one or more acts described in this detailed description can be implemented by one of ordinary skill in the art in light of the present disclosure and stored, e.g., on a computer-usable storage medium 179, which may be any device or medium that can store code and/or data for use by a computer system such as processor 172. The computer-usable storage medium 179 may be, but is not limited to, magnetic and optical storage devices such as disk drives, magnetic tape, compact discs, and DVDs (digital versatile discs or digital video discs). A communication port 177 may also be used to receive instructions that are used to program the computer 170 to perform any one or more of the functions described herein and may represent any type of communication connection, such as to the internet or any other computer network. Additionally, the functions described herein may be embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

Interference occurs when light scattered from the sample 110 is combined with coherent light. If the path difference between the combined probe beam and reference beam is varied, for example by providing relative motion between the sample 110 and the interferometric objective 140 in the perpendicular (Z) direction, then interference moves continuously between destructive minima and constructive maxima, and fringes in the resulting image are produced. Interference fringes are produced in both image-plane and pupil-plane detection. The coherence condition is satisfied by splitting the incident light into two paths, one of which reflects from the sample 110, sometimes referred to as the signal path, and the other reflects from a reference surface, sometimes referred to as the reference path. When light from the two paths is recombined, interference will occur when the light along the signal path and the reference path emanates from the same part of the light source 130 and when for all wavelengths present the optical path difference between the signal path and reference path varies by less than the coherence length of the light source. Maximum interference occurs when the optical path difference is the same at all wavelengths, which is not the same as requiring zero path difference.

A patterned target, such as that illustrated on sample 110, will potentially diffract incident light in multiple directions, so that the requirement of a common source point means that only the zero order diffracted light may form interference fringes from a spatially incoherent source. If the light source were truly monochromatic then the path difference will always be less than the source coherence length and the fringes will be seen for any value of path difference. With broader bandwidth light sources, fringes will be observed only for a small range of Z around the position where the optical path difference is the same at all wavelengths.

In the image plane, white-light interference fringes occur over only a very short path difference (approximately 2 μm for 400-800 nm wavelength illumination). Simple analysis of this signal allows for very precise determination of the location of the surface location in the Z axis and hence may be used as a focus indicator. Analysis of the variation of the focus position with location on the target surface allows measurement of the topography of the surface. Thus, optical metrology device 100 may use the image plane signal detection to locate pattern features and to focus the instrument.

As the system varies the path difference, e.g., scanning optical system 101 along the Z axis, a series of images are captured by the camera 160. The complete data set represents the signal I(X, Y, Z). The position Z should be known accurately for each captured image. If the position Z changes by a constant amount from one image to the next, analysis techniques, such as the Fast Fourier Transform, may be used for analysis of the frequency content of the signal. If the position Z is changed continuously, then the image will be changing during the integration time of the camera, and this must also be taken into account during analysis. A constant exposure time is desirable.

The optimum image spacing in Z, again expressed in terms of movement about the focal plane, is determined in part by the light source 130. For light with peak intensity at wavelength $\lambda$ the dominant spatial frequency of the interference fringe signal is approximately $\lambda/2$, so that for visible light illumination with $\lambda \approx 600$ nm the fringe period is approximately 300 nm. According to the Nyquist Theorem, full characterization of a signal with 300 nm period requires sampling at intervals of no less than 150 nm. A more rapid sampling, e.g., with physical spacing between points in a scan between 10 nm and 100 nm, may be beneficial to reduce the signal to noise ratio.

For light with bandwidth 400-900 nm, fringes from a single reflecting surface are observed if Z is within approximately 2 μm of the focal plane (Z=0). With patterned targets the fringe pattern extends over a much greater range of Z, often asymmetrically about the focal plane. A total change in Z, expressed as movement with respect to the focal plane, of 20 μm is normally sufficient to capture the full signal.

The time to perform a scan should be as short as possible, provided that the scanner motion remains uniform and image signal to noise is not adversely affected by short exposure times. The rate at which the system may scan is consistent with the rate at which a frame of data, i.e., a single image, can be collected. There are several related points to consider: (1) the speed at which the system can scan in Z, (2) the impact of scan rate on system vibration, (3) any variation in the Z change between images in the scan, (4) the ability to explicitly relate each acquired image to a Z position in the scan, and (5) the impact of system vibration on the frequency distribution of noise in the acquired signal. The scanner selection is germane to each of these points. In general, the scanner should operate in a closed loop mode possibly using error correcting closed loop motion in the axes perpendicular to the scan, i.e., a three axis stage with two slaved to compensate for the third. Internal sensors capable of recording the position of the scanner as it moves should be used. The scanner may use an electrical, piezoelectric, or magnetic drive system or a combination thereof. By way of example, a single axis piezoelectric scanner such as the P-625K018 Piezo Nanopositioning Stage manufactured by Physik Instrumente may be used.

Figure 5A:
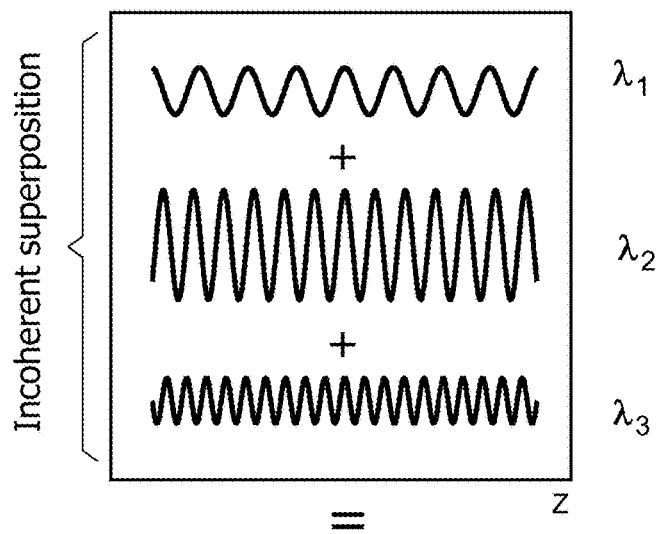
FIGS. 5A and 5B illustrate the superposition of multiple wavelength interference patterns.
Figure 5B:
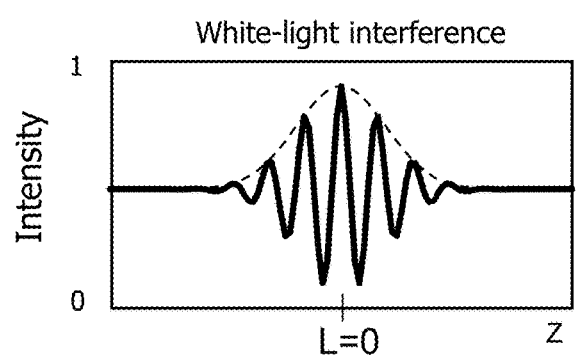
Figure 6A:
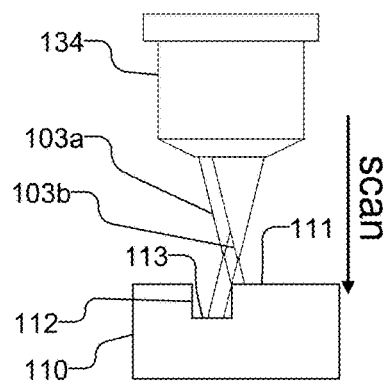
FIG. 6A illustrates beamlets of the illumination spot from an interferometric objective that are incident at different locations the sample.
Figure 6B:
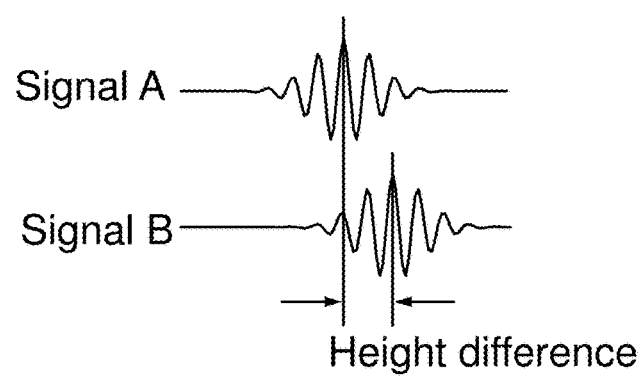
FIG. 6B illustrates a comparison of the signals from the beamlets illustrated in FIG. 6A.

In operation, the optical metrology device 100 scans the optical system 101, as indicated by the arrow 116, collecting interference patterns in the image plane. White light interference is the superposition of multiple wavelength interference patterns, as illustrated in FIGS. 5A and 5B. FIG. 5A, for example, illustrates the incoherent superposition of a plurality of wavelengths illustrated by $\lambda_1$, $\lambda_2$, and $\lambda_3$. FIG. 5B illustrates a combination of a plurality of wavelengths, e.g., including those illustrated in FIG. 5A, to produce a measured intensity of the light at a single pixel in camera 160, where the vertical axis represents intensity and the horizontal axis represents the Z position (i.e., height) from the surface of the sample 110. It will be understood by those skilled in the art, that FIGS. 5A and 5B are conceptual illustrations and that a curve such as that illustrated in FIG. 5B, generally requires a combination of more than three wavelengths such as that illustrated in FIG. 5A. In the image plane detection, when the peaks for the wavelengths are equal and all patterns have a common phase, the surface is detected (Z=0). By measuring multiple locations in the illumination spot, i.e., by detecting intensity signals for different pixels in camera 160, the height difference at the different locations can be determined. For example, FIG. 6A illustrates beamlets 103a and 103b of the illumination spot from interferometric objective 140 and that are incident at different locations the sample 110. By detecting the intensity signals in the image plane for the pixels in camera 160 associated with beamlets 103a and 103b, the height difference between the locations upon which beamlets 103a and 103b are incident may be determined. FIG. 6B illustrates, for example, a comparison of the Signal A, e.g., from beamlet 103a, and a Signal B, e.g., from beamlet 103b, where the difference between the intensity of Signal A and Signal B is directly related to the height difference between the locations upon which beamlets 103a and 103b are incident. By scanning the interferometric objective 140 parallel to the surface of the sample 110, the topography of the surface of the sample 110 can be mapped as a three-dimensional image. White light interferometry and its general operation are described in more detail in U.S. Pat. No. 5,398,113, which is incorporated herein by reference in its entirety.

In the pupil plane, each point (X, Y) in the pupil plane image corresponds to a single angle of incidence ($\phi$) and azimuth angle ($\theta$) for the incident beams. With knowledge of the position of the center of the pupil, and how to convert from a distance in pixels from the pupil center to an angle of incidence, analysis of the modulation of the signal I(X, Y, Z) at a point (X, Y) in the detection plane as Z is varied carries information about the zero order diffracted signal strength from the sample. The optical metrology device 100 therefore allows detection of the strength of zero order diffraction from the portion of the sample within the probe region as a function of angle of incidence and azimuth angles. Appropriate analysis of I(X, Y, Z) also allows spectral behavior to be extracted.

Since interference fringes are only observed for zero order diffracted light, it follows that a useful signal is obtained only for incident angles within the aperture of the illumination system. Using an objective with the highest possible numerical aperture (NA) and an illumination system with the same NA therefore provides the greatest possible range of useful angles of incidence, ϕ. Using an illumination system with an NA that is less than that of the objective will reduce the maximum incident angle that can be used in the system. Using an illumination system with a higher NA than the objective is undesirable because the highest angles will be blocked at the objective, and light incident at these blocked angles will potentially be scattered into the camera 160 and could introduce unwanted noise.

In pupil-plane detection the fringe signal at each point arises from light with unique incidence and azimuth angle. The range of angles used in analysis can therefore be reduced by restricting the image points processed to those within the desired range and so there is no adverse consequence from using the highest possible illumination NA.

At a point (X, Y) (or, equivalently (ϕ, θ)) in an image acquired by the camera 160 while optical metrology device 100 is in pupil-plane operation, a signal I(X, Y, Z) is obtained as the path difference is changed, along the Z axis. As discussed above, the path difference may be changed in several different ways, for example by moving the sample 110 perpendicular to the XY plane, by moving the interferometric objective 140, by moving the whole optical system 101 while keeping the sample 101 stationary, or by moving a reference mirror. By suitable analysis of the signals I(X, Y, Z), many properties of the sample 110 may be determined.

Figure 7:
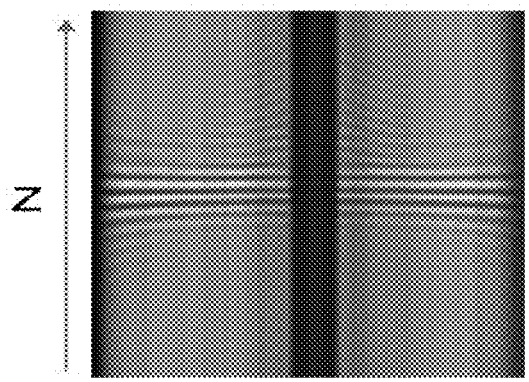
FIG. 7 illustrates an example of a frame of raw data collected from a sample with a grating using a scanning white-light interferometer operating in pupil plane mode.
Figure 8:
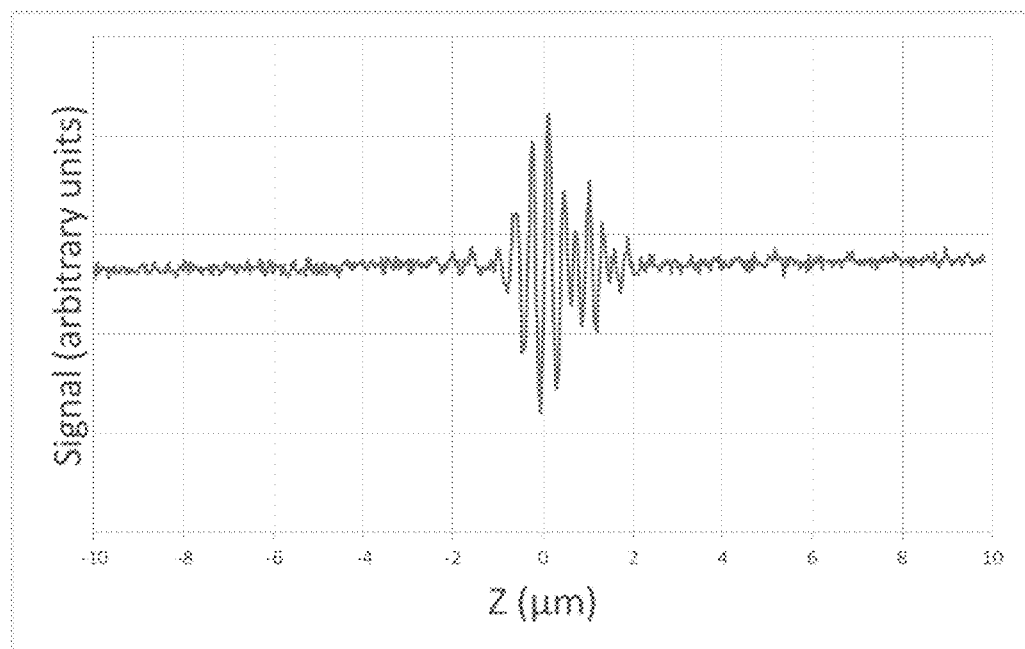
FIG. 8 illustrates the measured signal at a given pixel of the camera as a function of Z.

The raw output of the system is a cuboid of image data I(X, Y, Z) in physical XYZ space where the Z-axis represents a change in path difference between the signal and reference paths. The Z axis is normal to the wafer and thus to the top surface of the structure. The Z interval between successive images S(X, Y) may be constant and the collection of images by the detector should be tightly synchronized to the motion of the scanner. Each frame consists of the measurement of the optical intensity at each pixel of the detector in the camera 160. The data may be collected in the image plane, e.g., for focus detection and pattern recognition, or the pupil plane for characterization of the sample 110. FIG. 7 illustrates an example of the XZ plane of a raw cuboid of image data collected in the pupil plane from a sample with a silicon dioxide grating structure with pitch of 720 nm, bottom critical dimension of 180 nm, and thickness of 300 nm on a (100) Si substrate. The black area in the middle of FIG. 7 is due to the reference mirror in the Mirau objective, and Z=0, i.e., the focal plane, is approximately in the middle of the structure. FIG. 8 illustrates the measured signal at a given pixel of the camera as a function of Z.

The data may be analyzed by comparing the signal to a modeled signal and adjusting parameters in the model until the best fit is obtained. The parameters giving rise to the best fit are the desired measurement results. It is sometimes desirable to process the signal before the fit process to make the comparison more efficient, for example by performing a frequency analysis of the signal and/or by correcting for spatial variations in the light source across the illumination pupil. In another approach, an empirical analysis of the symmetry of the signal can be used to determine information about pattern asymmetry in the sample target. One application of this method, for example, is in the measurement of layer to layer overlay error, where displacement between two patterns printed in different lithography operations will introduce asymmetry into the signal. In another approach, comparisons may be made between an acquired set of data I(X, Y, Z) and a set acquired from a known good sample. Differences between the signals are indications that the test pattern is different from the golden pattern in some fashion. Appropriate characterization of the relationship between undesirable pattern changes and the changes seen in the detected signals allow identification of defective parts.

Figure 9:
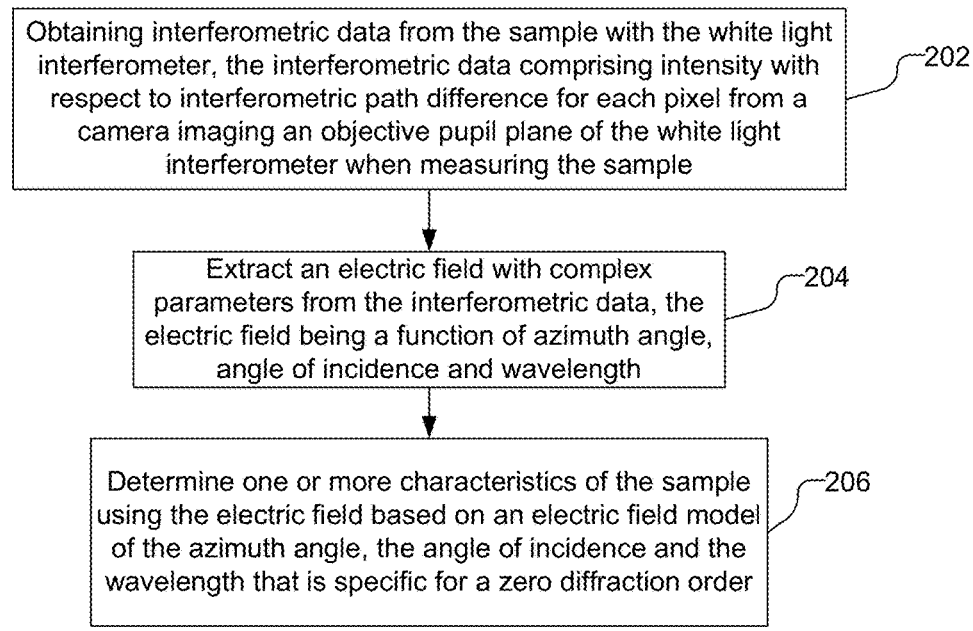
FIG. 9 is a flow chart illustrating a method of characterizing a sample with a white light interferometer.

FIG. 9 is a flow chart illustrating a method of characterizing a sample with a white light interferometer, such as the optical metrology device 100. As illustrated, interferometric data is obtained from the sample with the white light interferometer (202). The interferometric data includes the intensity with respect to optical path difference for each pixel from a camera imaging an objective pupil plane of the white light interferometer when measuring the sample. The interferometric data from the sample does not include non-zero diffraction orders. The interferometric data may be corrected for variation in source intensity at the pupil plane by obtaining intensity correction data, $C_1(X, Y)$, from a calibration sample, the intensity correction data comprising an intensity with respect to optical path difference for each pixel from the camera imaging the objective pupil plane of the white light interferometer when measuring the calibration sample; and adjusting the intensity with respect to optical path difference for each pixel from the camera using the intensity data correction for each respective pixel from the camera. The interferometric data may be obtained with the use of an output polarizer before the camera in the white light interferometer to suppress effects of undesired depolarization caused by optical elements in the white light interferometer.

In one implementation, the interferometric data is obtained by generating an illumination beam of broadband light; using a beam splitter to direct the illumination beam through an aperture stop at the objective pupil plane; polarizing the illumination beam; using an interferometric objective lens to cause the illumination beam to be incident on the sample, wherein the illumination beam is reflected off the sample to produce a reflected beam; receiving the reflected beam with the interferometric objective lens to direct the reflected beam towards the beam splitter; polarizing the reflected beam; using the beam splitter to direct the reflected beam towards the camera; focusing an image of the objective pupil plane on the camera; polarizing the reflected beam after the beam splitter directs the reflected beam towards the camera and before the reflected beam is received as an image of the objective pupil plane by the camera; wherein the camera captures images of the objective pupil plane while the interferometric objective lens varies the optical path difference. Additionally, the illumination beam may be diffused prior to passing through the aperture stop at the objective pupil plane to reduce variation in intensity at the pupil plane.

An electric field with complex parameters is extracted from the interferometric data, the electric field being a function of azimuth angle, angle of incidence and wavelength (204). The electric field with complex parameters from the interferometric data may be extracted by performing a Fourier transform of the interferometric data at each pixel. The electric field for example, may be extracted by converting each pixel from the camera imaging the objective pupil plane into a unique set of angle of incidence and azimuth angle of light incident on the sample, e.g., before or after performing a Fourier transform. Additionally, each set of angle of incidence and spatial frequency from the Fourier transform may be converted to a wavelength. Converting each pixel from the camera imaging the objective pupil plane into the unique set of angle of incidence and azimuth angle of light incident on the sample may be performed by determining a center of the objective pupil plane using the interferometric data from the sample, and determining the unique set of angle of incidence and azimuth angle of the light incident on the sample for each pixel from the camera based on the center of the objective pupil plane.

One or more characteristics of the sample is determined using the electric field based on an electric field model of the azimuth angle, the angle of incidence and the wavelength that is specific for a zero diffraction order (206). The electric field model may be represented as a generalized Jones matrix. The one or more characteristics of the sample may be determined by fitting the electric field extracted from the interferometric data to the electric field model. The measured signal $F(\phi, \theta, k)$ may be considered as a simple product of the electric field model $E_{out}(\phi, \theta, k)$ and a contribution $P(\phi, \theta, k)$ to the measured signal arising from tool effects, i.e., imperfections in the tool that are not directly included in electric field model. Thus, it is desirable to characterize and correct for the tool effects $P(\phi, \theta, k)$ arising from imperfections in the tool that are not directly included in electric field model $E_{out}(\phi, \theta, k)$. The tool effects $P(\phi, \theta, k)$ that contribute to the measured signal $F(\phi, \theta, k)$ may arise from many sources including, but not limited to, spatial and spectral distribution of the light source, variations in optical component reflection and transmission with position and wavelength, depolarizing elements, relative phase retardation with path through the optical system, misalignment, and spatial and spectral variation in detector sensitivity. The electric field extracted from the interferometric data may be corrected for the variation $C_2(X, Y, k)$ in source intensity with spatial frequency, and with position within the pupil plane, $(X, Y)$, or by its variation $C_3(\phi, \theta, k)$ with spatial frequency, angle of incidence and azimuth angle. The term $C_2(X, Y, k)$ can only include spectral terms in k if the relationship between position within the image, $(X, Y)$, and angle location within the pupil, $(\phi, \theta)$ is known because the relationship $K=2 k \cos \phi$ is required in applying it. The electric field model, for example, may include contributions from a model sample, including one or more variable parameters, as well as from a model white light interferometer, including a diattenuation model for optical components of the white light interferometer and any variation $C_4(\phi, \theta, k)$ in the total source intensity with wavelength and intensity and phase distribution in the objective pupil plane of the light source for the white light interferometer, i.e., tool effects $P(\phi, \theta, k)$, that has not been corrected for in the electric field determined from the interferometric data. Correction or modeling of the source distribution can be distributed among any of the four correction functions, with the intent to allow for all of the actual source variation, so that $C_1(X, Y) \cdot C_2(X, Y, k) \cdot C_3(\phi, \theta, k) \cdot C_4(\phi, \theta, k) = P(\phi, \theta, k)$. The choice of function $C_1$ through $C_4$ used to correct a particular source of unwanted signal variation in $P(\phi, \theta, k)$ may advantageously be made depending on the origin of the contribution. For example, camera pixel sensitivity might be corrected using $C_1(X, Y)$ if it is independent of wavelength, or using $C_2(X, Y, k)$ if it is wavelength dependent. Alternatively, the one or more characteristics of the sample may be determined using a library for the electric field model of the azimuth angle, the angle of incidence and the wavelength.

Figure 10:
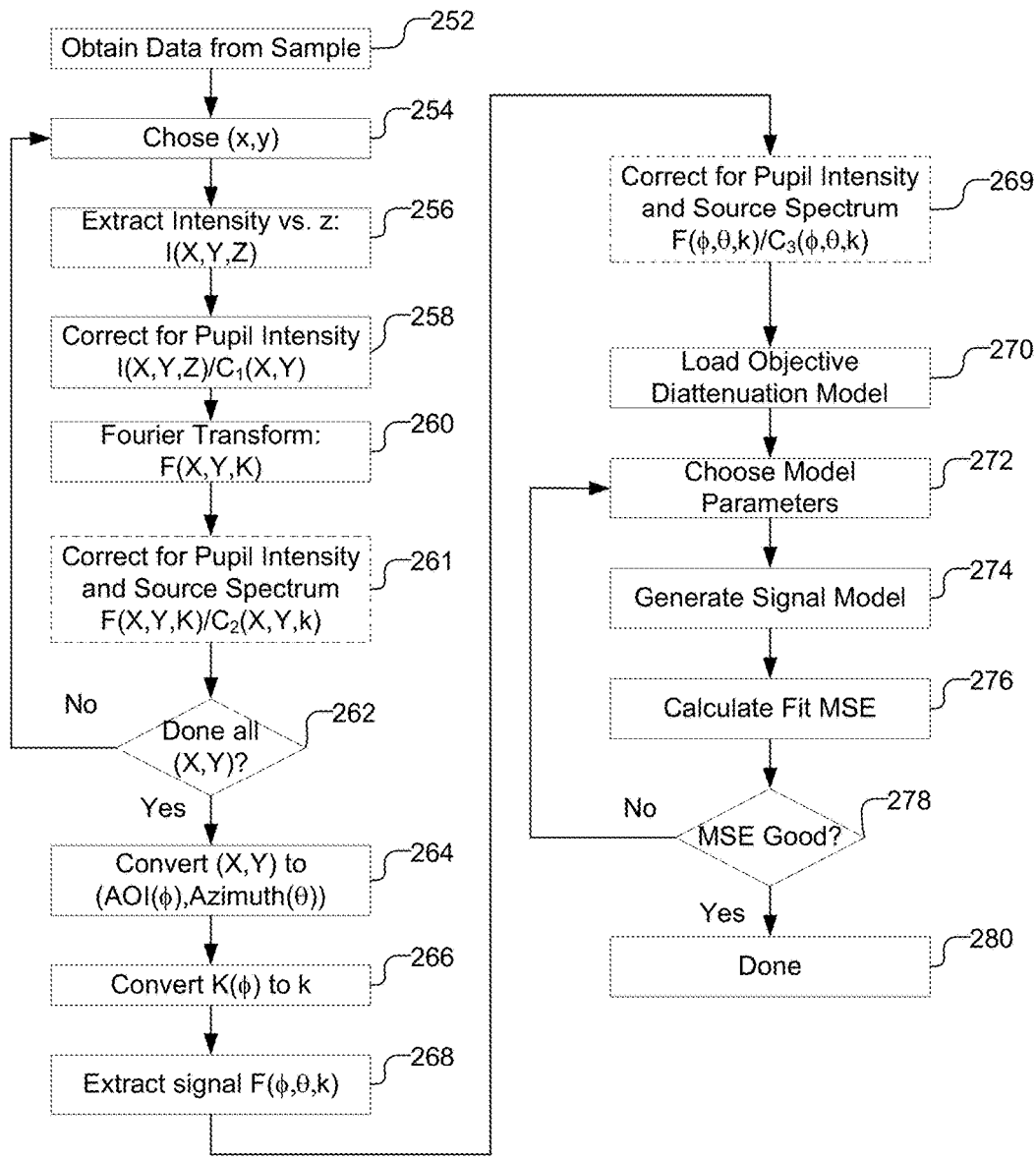
FIG. 10 is another flow chart illustrating an approach used to analyze the data that has been collected by the optical metrology device.

FIG. 10 is another flow chart illustrating an approach used to analyze the data that has been collected by the optical metrology device 100. As illustrated, the data measured from the sample 110 is obtained (252). For a selected pixel $(X, Y)$ of the camera 160 (254), the intensity with respect to Z, $I(X, Y, Z)$ is extracted (256), resulting in a signal similar to that shown in FIG. 8. The intensity signal with respect to Z may be corrected for variation in intensity at the pupil plane (258). As discussed above, the intensity of the input beam at the entry to the aperture stop 108 should be uniform, which the use of the diffuser 112 greatly assists. Nevertheless, some variation in the intensity at the aperture stop 108 due to the light source 130 and optical system is likely and this variation in pupil intensity is to be corrected. A calibration measurement of the pupil plane may be performed using a calibration sample, e.g., a sample having a smooth surface with a known film and material properties so that the model can be used to determine the reflectance of the sample, to produce an intensity correction signal $C_1(X, Y)$ and the intensity signal with respect to Z is corrected with the intensity correction signal, i.e., $I(X, Y, Z)/C_1(X, Y)$ (258). Alternatively, the variation in the signal intensity and phase at the pupil plane may be corrected at a different point in the analysis, or be included in the model, or be allowed for by a combination of correction and model terms As illustrated in FIG. 10, a Fourier transform is applied to the resulting corrected signal at the current pixel, to produce a Fourier transformed signal $F(X, Y, K)$ (260), where K is the transform spatial frequency. As discussed above, by generating the data by changing the Z position by a constant amount from one image to the next, a Fast Fourier Transform may be used. The extraction of the intensity, correction for pupil intensity, and Fourier transform is performed for all desired pixels $(X, Y)$ of the camera (262).

The data may be transformed into data sets with a given angle of incidence (AOI) $(\phi)$ and azimuth angle $(\theta)$ by converting $(X, Y)$ to $(\phi, \theta)$ (264). The data is transformed by determining a center of the objective pupil plane using the interferometric data from the sample, and determining the unique set of angle of incidence and azimuth angle of the light incident on the sample for each pixel from the camera based on the center of the objective pupil plane. A full range of azimuthal $\theta$ angles is used as the modeling is performed in the electric field space. If the modeling used reflectance instead of the electric field, only a portion of the azimuthal range would be required for some samples, e.g., unpatterned samples. Additionally, the data is transformed into data sets with a given wavelength by converting the spatial frequency K and angle of incidence $(\phi)$ to k (266). The signal Fourier transform at a specific angle of incidence, $\phi$, has a frequency term of $K=2 k^*\cos(\phi)$, rather than simply k (k is the spatial frequency of the light source, $k=2\pi/\lambda$), so that after the Fourier transform in Z, each slice in "frequency" space does not correspond to a single inverse wavelength. Accordingly, a pixel by pixel interpolation is used to obtain the transformed signal as a function of AOI and azimuth angle at a constant wavelength. The resulting signal $F(\phi, \theta, k)$ is extracted (268), which can then be fit to a model.

Figures 11A, 11B:
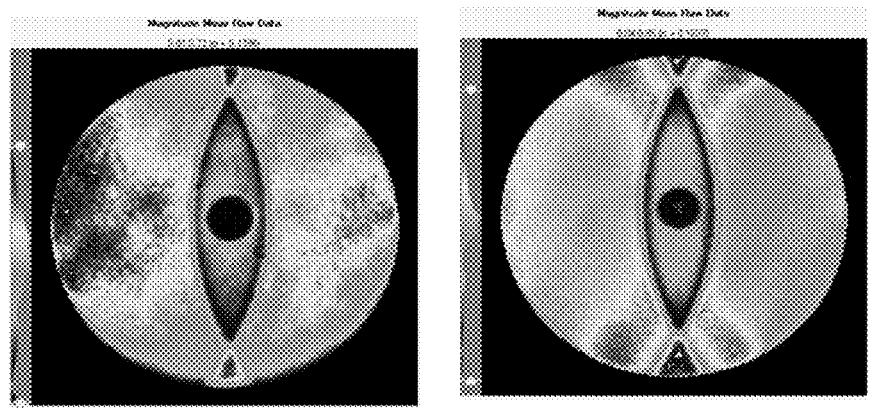
FIGS. 11A and 11B illustrate the removal of the variation in intensity across the pupil plane.

As discussed above, the extracted signal may be corrected for variation in intensity and phase in the pupil plane before the signal is transformed, e.g., in step 258. If desired the signal may be corrected for variation in intensity and phase after transformation. For example, the transformed signal may be corrected for variation in signal intensity and phase, $C_2(X, Y, k)$, using previously determined calibration data, as illustrated in step 261. This correction may be in addition to or in place of correction to the signal with respect to Z (258)

using measured function $C_1(X, Y)$ at step 258. FIGS. 11A and 11B, for example, illustrate the removal of the variation in source intensity across the pupil plane from the transformed signal, where FIG. 11A illustrates the raw intensity data at $Z=0$ in the XY plane, and FIG. 11B illustrates the intensity data shown in FIG. 11A, but with the pupil intensity variation removed. If desired, the correction may be determined as a function of angle of incidence ($\phi$) and azimuth angle ($\theta$) instead of or in addition to correction using the function $C_2(X, Y, k)$ and applied as a function $C_3(\phi, \theta, k)$ to the signal after conversion of the co-ordinate systems, as illustrated in step 269. Alternatively, some or all of the correction may be included as a function $C_4(\phi, \theta, k)$ that is used in the system model discussed below and corrections $C_1(X, Y)$, $C_2(X, Y, k)$, $C_3(\phi, \theta, k)$ need not be applied in the process illustrated in FIG. 10. It should be apparent that while correction for the source spectrum and distribution can be applied in more than one place within the process illustrated in FIG. 10, a correction that is applied in one step should not be applied again in another step. For example, one correction, e.g., $C_2(X, Y, k)$ may be used to correct for variation in camera pixel sensitivity, while another correction $C_3(\phi, \theta, k)$ may be used for everything else. Consequently, the net effect of applying one or more of the corrections $C_1(X, Y)$, $C_2(X, Y, k)$, $C_3(\phi, \theta, k)$ and $C_4(\phi, \theta, k)$ is an approximation to the components of the optical metrology tool effects $P(\phi, \theta, k)$, not allowed for in other ways.

To fit the signal $F(\phi, \theta, k)$ to a model, a model for the optical metrology tool effects $P(\phi, \theta, k)$ as well as the sample is generated. Some components of the optical metrology tool model effects $P(\phi, \theta, k)$ may advantageously be included directly in the electric field model. For example, a diattenuation model of the optical system is loaded (270). The diattenuation model models the diattenuation in the system components of the optical metrology tool, such as the beam splitter and interferometric objective 140 and may include variable parameters, such as the angle of polarizers 138 and 158. The diattenuation model may have several embodiments. For example, the diattenuation model may include a limited number, e.g., five, parameters, such as the two polarizer angles for polarizers 138 and 158, the percent of transmission and reflection from the beam splitter 144 in objective 140 (e.g., 50/50 at all AOIs may be a baseline), and the reflectivity of the reference mirror 146 in the objective 140 (e.g., 100% at all AOIs may be a baseline). However, if desired, the diattenuation model may include a greater number of parameters. For example, the diattenuation model may include a thin film stack model for the reference mirror 146 and/or the top and bottom surface of the beamsplitter 144. For example, with the use of a thin film stack model, each film added will include a further thickness and optical dispersion. The optical dispersion may be either taken from a fixed lookup table or floated using one of the variety of optical dispersion models. The complexity of the diattenuation model is limited largely by the knowledge of the actual construction of the objective 140. Accordingly, a simple diattenuation model may be used with complexity added as fidelity of the data improves. The diattenuation model may be pre-generated in a calibration phase, e.g., by measuring a calibration sample with the optical metrology device and comparing the measured signals to signals modeled based on an ideal optical metrology device measuring the known sample, and determining variations from the ideal optical metrology device that is necessary to match the measured signals. Sample model parameters are chosen (272) and a model of the signal is generated based on the selected parameters and the diattenuation model (274). By way of example, the signal model may be generated using Rigorous Coupled Wave Analysis (RCWA) or other appropriate techniques. A comparison between the extracted signal and the modeled signal is performed to calculate the Mean Square Error (MSE) of the fit (276). New model parameters are selected and the fitting process repeats until an MSE that is considered good (278), e.g., within a specified tolerance or the best MSE, is found and process if finished (280) with the parameters giving rise to the best fit are the desired measurement results. The measurement results may be stored in relation to the sample or provided to an end user.

If desired, as described previously, the experimental data can be processed in stages to remove some or all of the distortions and transformations introduced by the metrology device using one or more of the correction functions $C_1(X, Y)$, $C_2(X, Y, k)$ and $C_3(\phi, \theta, k)$, e.g., at one or more of steps 258, 261, and 269 illustrated in FIG. 10. The model data can be processed in stages to generate a simulation of data collected by the metrology device. The extent to which the tool data and system model are transformed before a comparison of the fit between the two is made can be varied, as long as the appropriate number of transformations are made to each to bring them to the same place in the model of the relationship between the raw data and the system model. The fit can be performed after processing using various schemes. For example, as illustrated in FIG. 10, the raw signal can be processed to remove or reduce the tool effects $P(k, \phi, \theta)$, resulting in a corrected spatial frequency map $F'(\phi, \theta, \lambda)$. The model signal generated at 274 to match this signal excludes allowance for the distribution of illumination in the pupil plane. In some cases, such as if the sample 110 is unpatterned, the size of the corrected signal data $F'(k, \phi, \theta)$ can be reduced significantly by fitting to a model of the behavior of the target reflectance, especially as a function of azimuth angle $\theta$.

In another method, a system model can be used to predict a raw signal $I(X, Y, Z)$, including effects such the source spectrum, distribution of illumination in the pupil plane, absorption and scattering losses at each optical component and polarization effects of components such as the objective. In another example, the raw signal $I(X, Y, Z)$ can be converted to a spatial frequency map $F(k, \phi, \theta)$ without correcting for the source spectral and spatial distribution. The system model can be processed as discussed above, but will include all tool effects such as the source spectrum, distribution of illumination in the pupil plane, absorption and scattering losses at each optical component and polarization effects of components such as the objective.

In developing a system level model, the electric field is used directly rather than the intensity because phase information is relevant in interferometry systems. To this end, a Jones matrix formalism is adopted. Operation in the pupil plane demands that the components of the Jones matrix have an inherent positional dependence. The formulation of the system level model depends explicitly on the number and position of the polarizers relative to the other optical components.

As an example, as illustrated in FIGS. 1 and 2, the optical metrology device 100 uses a single polarizer 138 that is positioned above the interferometric objective 140, wherein light from the light source 130 enters the interferometric objective 140 after passing through the polarizer 138 and reflected light returning from the sample 110 renters the same polarizer 138. Thus, there are two instances of polarization of the light, wherein the instances of polarization have the same orientation. The polarizer 158 in the detection arm of the optical metrology device 100 is used to remove changes in polarization to the reflected light from the sample 110 due to the intervening optical system between the polarizer 138 and the camera 160.

A number of other physical realizations of two polarizers may be used with optical metrology device 100. For example, in one instance, a polarizer 138a shown in FIG. 1 may be placed between the light source 130 and the beam splitter 136 that separates the detection arm from the interferometric objective 140, and another polarizer 138b may be placed in the detection arm. In this instance, light passes through each polarizer 138a and 138b once, and thus, the relative orientations of the two polarizers 138a and 138b should be known. In another instance, polarizer 138 positioned at the input of the interferometric objective 140 may be used along with polarizer 138b in the detection arm, wherein light passes through the first polarizer 138 twice and passes through the second polarizer 138b once. Again, the relative orientations of the two polarizers 138 and 138b should be known.

The electric field system model may be generated based on the following assumptions: depolarization induced by the optical elements is ignored, the polarizers are assumed to be ideal, the input light is completely unpolarized, the diattenuation of the Mirau objective dominates the system, and the beam splitters in the Mirau objective are thin enough to ignore the lateral offset of a ray after transmission. Each of these assumptions may be removed to improve the system model as desired. Under these assumptions and using the geometric conventions illustrated in FIGS. 4A and 4B, the out coming electric field vector for the rays that strike either the reference mirror 146 or sample 100 for the configuration of the optical metrology device 100 with the polarizer 138 or for a configuration with two polarizers 138a and 138b, may be written in matrix form as follows.

$$E_{Out} = P(\gamma_2) R_z(-\theta) t_{BS2} R S t_{BS1} R_z(\theta) P(\gamma_1) E_{In} \quad \text{(Eq. 1)}$$

where each of the terms is described in the following table 1.

TABLE 1

| | |
|---|---|
| $E_{In} = \begin{bmatrix} e1 \\ 0 \end{bmatrix} + \begin{bmatrix} 0 \\ e2 \end{bmatrix}$ | Electric field vector (incoherent superposition) |
| $P(\gamma) = \begin{bmatrix} \cos^2(\gamma) & \sin(\gamma)\cos(\gamma) \\ \sin(\gamma)\cos(\gamma) & \sin^2(\gamma) \end{bmatrix}$ | Jones Matrix for Linear Polarizer |
| $R_z(\theta) = \begin{bmatrix} \cos(\theta) & \sin(\theta) \\ -\sin(\theta) & \cos(\theta) \end{bmatrix}$ | Rotation matrix |
| $t_{BSx} = \begin{bmatrix} t_{px} & 0 \\ 0 & t_{sx} \end{bmatrix}$ | Jones Matrix for beamsplitters (central source of diattenuation) |
| $S = \begin{bmatrix} r_{pp} & r_{ps} \\ r_{sp} & r_{ss} \end{bmatrix}$ | Jones Matrix of the sample or reference |
| $R = \begin{bmatrix} 1 & 0 \\ 0 & -1 \end{bmatrix}$ | Reflection Matrix |

In the general case, the incident electric field $E_{In}$ will vary with spatial frequency, k, as well as with position in the pupil, that is with $\phi$ and $\theta$. The functions $e1(k, \phi, \theta)$ and $e2(k, \phi, \theta)$ can be determined experimentally. Alternatively, the model can treat the electric field as independent of $\phi$ and $\theta$ if the pupil illumination is known to be perfectly uniform, or if the signal with which the model is compared is corrected for variation with $\phi$ and $\theta$. Similarly, the model can be treated as independent of k if it is compared with a signal that is corrected for the source spectrum.

Additionally, the model includes contributions from the sample, S, as well as the polarizers and the beamsplitter. The objective beamsplitter introduces diattenuation through the term t. Incident light passes through objective beamsplitter twice, once in the direction of the sample and again after reflection from the sample, and so equation 1 includes two beamsplitter terms, which are identified as $t_{BS1}$ and $t_{BS2}$ for generality. Each polarizer is represented by a rotation term Rz.

It is helpful to rewrite (Eq. 1) as:

$$E_{Out} = M(\gamma_2, \gamma_1) E_{In} = P(\gamma_2) A P(\gamma_1) E_{In} \text{ with} \quad \text{(Eq. 2)}$$

$$A = \begin{bmatrix} A_{11} & A_{12} \\ A_{21} & A_{22} \end{bmatrix}$$

where the elements of A are:

$$A_{11} = t_{p1} t_{p2} r_{pp} \cos^2 \theta - t_{s1} t_{s2} r_{ss} \sin^2 \theta + (t_{p1} t_{s2} r_{sp} - t_{s1} t_{p2} r_{ps}) \sin \theta \cos \theta \quad \text{(Eq. 3.1)}$$

$$A_{12} = t_{p1} t_{s2} r_{sp} \sin^2 \theta + t_{s1} t_{p2} r_{ps} \cos^2 \theta + (t_{p1} t_{p2} r_{pp} + t_{s1} t_{s2} r_{ss}) \sin \theta \cos \theta \quad \text{(Eq. 3.2)}$$

$$A_{21} = -t_{p1} t_{s2} r_{sp} \cos^2 \theta - t_{s1} t_{p2} r_{ps} \sin^2 \theta + (t_{p1} t_{p2} r_{pp} + t_{s1} t_{s2} r_{ss}) \sin \theta \cos \theta \quad \text{(Eq. 3.3)}$$

$$A_{22} = t_{p1} t_{p2} r_{pp} \sin^2 \theta - t_{s1} t_{s2} r_{ss} \cos^2 \theta - (t_{p1} t_{s2} r_{sp} - t_{s1} t_{p2} r_{ps}) \sin \theta \cos \theta \quad \text{(Eq. 3.4)}$$

If $\gamma_1$ and $\gamma_2$ are either P or S linearly polarized. i.e., 0° or 90° respectively, it can be shown that the matrix M is:

$$M(p, p) = \begin{bmatrix} A_{11} & 0 \\ 0 & 0 \end{bmatrix}, M(p, s) = \begin{bmatrix} 0 & A_{12} \\ 0 & 0 \end{bmatrix}, \quad \text{(Eq. 4)}$$

$$M(s, p) = \begin{bmatrix} 0 & 0 \\ A_{21} & 0 \end{bmatrix}, M(s, s) = \begin{bmatrix} 0 & 0 \\ 0 & A_{22} \end{bmatrix}$$

which implies that each element of the A matrix is associated with a particular combination of input and output polarizer combinations. The general solution of the output electric field which covers the configurations the optical metrology device 100 with the polarizer 138 or with two polarizers 138a and 138b:

$$E_{Out} = E_{In} \frac{g(\gamma_2, \gamma_1)}{2} \begin{bmatrix} \cos(\gamma_1)(\cos(\gamma_2) + \sin(\gamma_2)) \\ \sin(\gamma_1)(\cos(\gamma_2) + \sin(\gamma_2)) \end{bmatrix} \quad \text{(Eq. 5.1)}$$

$$g(\gamma_2, \gamma_1) = \cos(\gamma_1)(A_{11} \cos(\gamma_2) + A_{12} \sin(\gamma_2)) + \sin(\gamma_1)(A_{21} \cos(\gamma_2) + A_{22} \sin(\gamma_2)) \quad \text{(Eq. 5.2)}$$

However, the configuration of the optical metrology device 100 with the polarizer 138 implies that $\gamma_1 = \gamma_2 = \gamma$ which implies (Eq. 5.1) and (Eq. 5.2) to:

$$E_{Out} = E_{In} \frac{f(\gamma)}{8} \begin{bmatrix} 1 + \cos(2\gamma) + \sin(2\gamma) \\ 1 - \cos(2\gamma) + \sin(2\gamma) \end{bmatrix} \quad \text{(Eq. 6.1)}$$

$$f(\gamma)=A_{11}+A_{22}+(A_{11}-A_{22})\cos(2\gamma)+(A_{12}-A_{21})\sin(2\gamma)=g(\gamma,\gamma) \quad \text{(Eq. 6.2)}$$

If the optical metrology device 100 has the configuration with polarizer 138 positioned at the input of the interferometric objective 140 and polarizer 138b positioned in the detection arm, (Eq. 1) is altered to include another polarizer Jones matrix, which written in terms of (Eq. 2) and keeping the already defined M and A matrices the same would be in the most general case be written:

$$E_{Out}=P(\gamma_3)M(\gamma_2,\gamma_1)E_{In}=P(\gamma_3)P(\gamma_2)AP(\gamma_1)E_{In} \quad \text{(Eq. 7)}$$

However, the configuration with polarizer 138 and polarizer 138b implies that $\gamma1=\gamma2=\gamma$, and it can be shown that the resultant electric field vector will have the form:

$$E_{Out} = E_{In}\frac{f(\gamma)}{4}\begin{bmatrix} \cos(\gamma-\gamma_3)\cos(\gamma_3)(\sin(\gamma)+\cos(\gamma)) \\ \cos(\gamma-\gamma_3)\sin(\gamma_3)(\sin(\gamma)+\cos(\gamma)) \end{bmatrix} \quad \text{(Eq. 8)}$$

If $\gamma1=\gamma2=\gamma3=\gamma$, (Eq. 8) will reduce to (Eq. 6.1), but there are practical implications to this configuration. Small misalignments of the polarizer 138 above the interferometric objective 140 are possible and could give rise to a signal at the camera 160 that has a mixture of polarizations. The use of a second polarizer 158 in the detector arm minimizes the impact of small misalignment error. Also, the second polarizer 158 can help eliminate spurious depolarization which, although it has been assumed to not be a factor, in fact, may be a factor.

While linear polarized light has been the focus of the present disclosure, the use of circularly polarized light has some interesting implications for the system model. The M matrix when two right circular polarizers are used would be:

$$M(RCP, RCP) = \begin{bmatrix} (A_{11}+A_{22})+i(A_{21}-A_{12}) & i(A_{11}+A_{22})-(A_{21}-A_{12}) \\ -i(A_{11}+A_{22})+(A_{21}-A_{12}) & (A_{11}+A_{22})+i(A_{21}-A_{12}) \end{bmatrix} \quad \text{(Eq. 9)}$$

$$\text{with } P(RCP) = \frac{1}{2}\begin{bmatrix} 1 & i \\ -i & 1 \end{bmatrix}$$

This result is interesting because there are no azimuthal terms and the combinations of the elements of the A matrix reduce to:

$$A_{11}+A_{22}=t_{p1}t_{p2}r_{pp}-t_{s1}t_{s2}r_{ss} \quad \text{(Eq. 10.1)}$$

$$A_{21}-A_{12}=-(t_{p1}t_{s2}r_{sp}-t_{s1}t_{p2}r_{ps}) \quad \text{(Eq. 10.2)}$$

Use of a two left circular polarizers yields a similar result. There are several potential benefits of having no azimuthal dependence including the ability to consider only one quadrant to decrease signal acquisition or to average the four quadrants together as a way of improving the signal to noise ratio.

Given the form of the electric field based on linear polarization, the raw signal at the detector, i.e., before a Fourier transform is performed, can be calculated with:

$$I(\phi, \theta, z) = \sum_k |E_{Out}(\phi, \theta, k)e^{2ik\cos(\varphi)z} + E_{Ref}(\phi, \theta, k)|^2 \Delta k \quad \text{(Eq. 11)}$$

where $\theta$ and $\phi$ are defined as in FIGS. 4A and 4B, $E_{Out}$ and $E_{Ref}$ are the outgoing electric fields from the path containing the sample 110 and the reference mirror 146, and are both proportional to the incident field $E_{In}$, k is the wavevector ($k=2\pi/\lambda$, where $\lambda$ is the source wavelength), and z is the path difference between the sample and reference beams wherein z=0 implies these two paths are matched.

As previously discussed, data for a sample 110 is collected by scanning along the z-axis and in turn taking the Fourier transform of the resulting signal at each pixel, as illustrated in the flow chart of FIG. 10. Inspection of (Eq. 11) demonstrates that only the cross terms will yield a non-zero result and only one of those cross-terms will be relevant if only the positive or negative frequencies from the Fourier transform are kept. Accordingly, the transformed signal will take the form:

$$FT[I(\phi,\theta,z)](\phi,\theta,k) \propto E_{Ref}(\phi,\theta,k)E_{Out}(\phi,\theta,k)^\dagger \quad \text{(Eq. 12)}$$

When comparing the above signal model from (Eq. 12) to the experimental signal, e.g., at step 276 in FIG. 10, a complex proportionality factor may be used. Again referring back to (Eq. 11) it should be clear that the magnitude of the FT[Signal] is modulated by the spectral and spatial variation in the incident field, $E_{in}$. The spectral and spatial variation of $E_{in}$ may be treated as independent functions, that is we may use $$E_{In}=E_0(t)\sqrt{P(\phi,\theta,k)}=E_0(t)\sqrt{V(k)P'(\phi,\theta)} \quad \text{(Eq. 13)}$$

where $E_0(t)$ includes only time-varying changes to intensity and is constant for all signals acquired at the same time, V(k) is the source spectrum and $P'(\phi, \theta)$ the source spatial variation in the pupil plane. This factorization is useful because V(k) and $P'(\phi, \theta)$ may be estimated separately, but there is some loss of generality if the path through the optics modifies the spectral content of $E_{In}$, e.g. when coatings are used for which transmission changes with angle of incidence and wavelength. The phase term is derived from the exponential term in (Eq. 11), i.e., $2 k \cos(\phi)z$, and the z value will depend on how the real space data was wrapped prior to the application of the Fourier transform, e.g., if it is wrapped to zero, z will be zero. Additionally, it should be noted that the dependent variable in the Fourier transform is $2 k \cos(\phi)$. Accordingly, a factor of $\cos(\phi)$ will modulate the amplitude of the signal resulting from this change in variable. Therefore, (Eq. 12) may be rewritten as:

$$FT[I(\phi,\theta,z)](\theta,\varphi,k)=[\cos(\phi)e^{2ik\cos(\varphi)}]\times E_{Ref}(\theta,\phi,k)E_{Sam}(\theta,\phi,k)^\dagger \quad \text{(Eq. 14)}$$

Thus, the signal from (Eq. 12) is the kernel of step 268, and the signal from (Eq. 13) is the final form from step 268 including the phase and magnitude scaling terms.

Figure 12A:
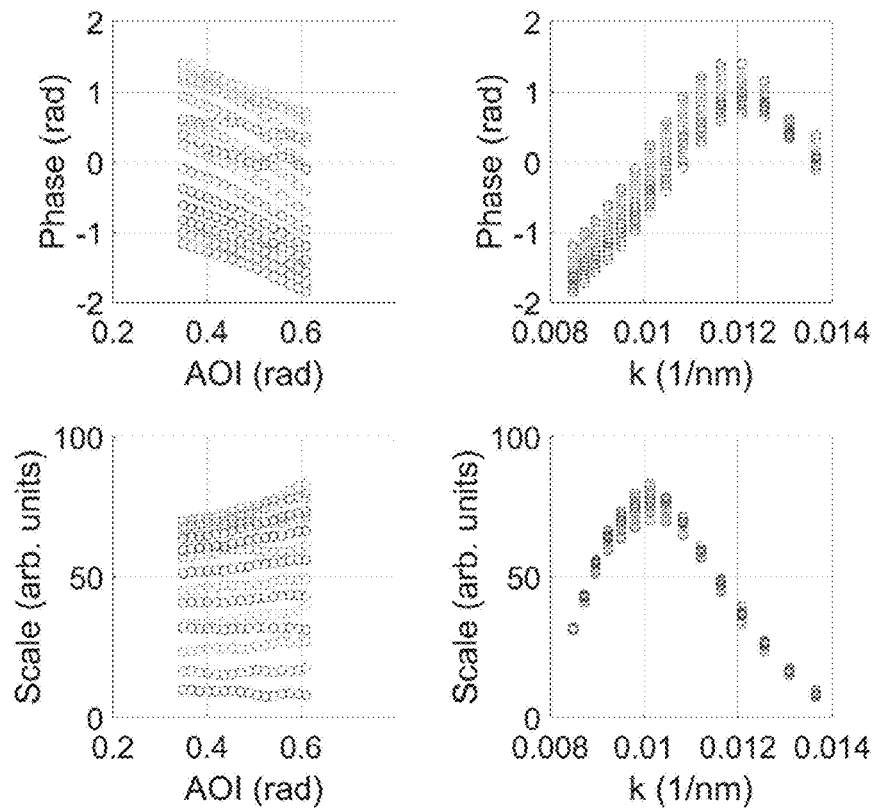
FIGS. 12A and B illustrates plots of a complex scaling factor (magnitude and phase) of raw data to a model for a grating.
Figure 12B:
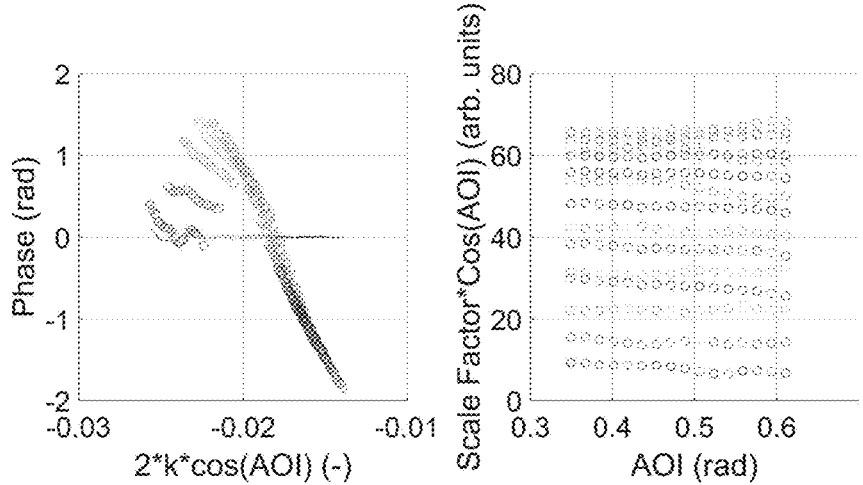

FIGS. 12A and B illustrates a demonstration of the behavior of experimental data collected with the optical metrology device 100 and the system model from (Eq. 14) based on a configuration with the polarizer 138. FIGS. 12A and B illustrates plots of a complex scaling factor (magnitude and phase), proportional to $P(\phi, \theta, k)$, of raw data to a model for a silicon dioxide grating with pitch of 360 nm, bottom critical dimension of 180 nm, and thickness of 300 nm on a (100) Si substrate. FIG. 12A plots the magnitude of the scale and phase against the angle of incidence (AOI) and wavevector (k). FIG. 12B, the phase is plotted against 2 k $\cos(\phi)$, and scale*$\cos(\phi)$ is plotted against angle of incidence, yielding simple linear results. It is noted that the phase behavior for some of the data does not follow the linear relationship between the phase and 2 k $\cos(\phi)$. That data was collected at the edge of the spectrum of the light source where the signal was very weak. Verifying the behavior of the scaling of the proportionality factor is a good way to validate that the measured data is within a generally useful range.

Figure 13A:
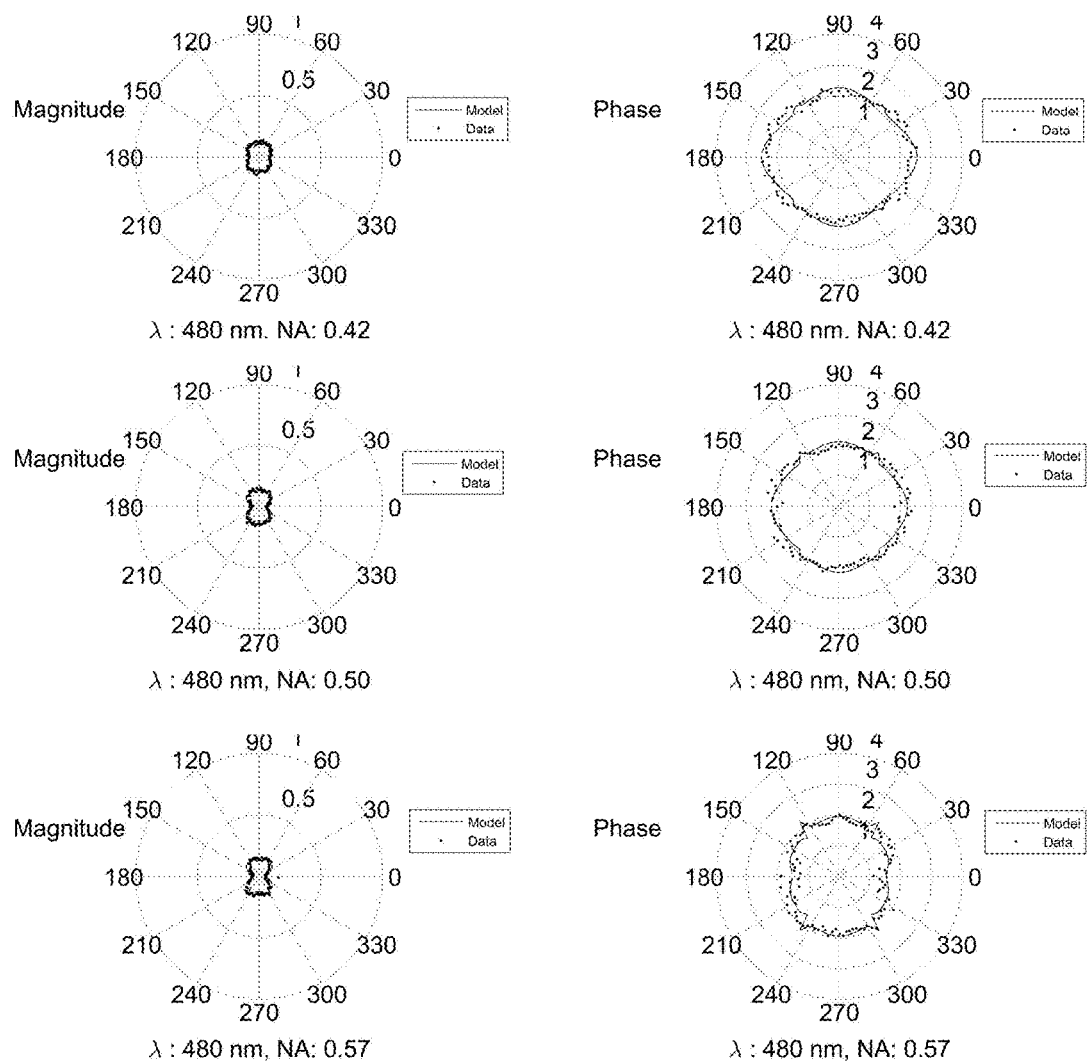
FIGS. 13A, 13B, and 13C are illustrations of the application of a model to data collected by the scanning white-light interferometer.
Figure 13B:
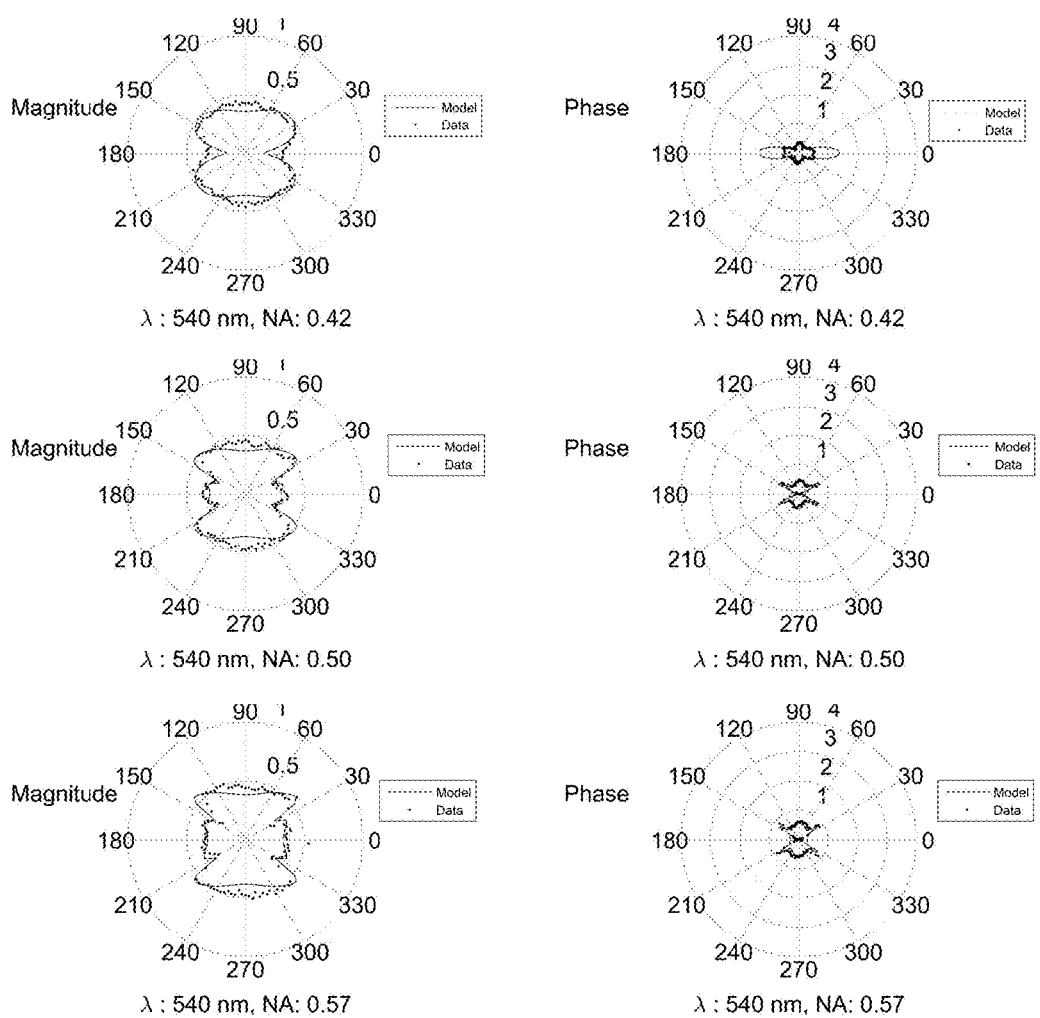
Figure 13C:
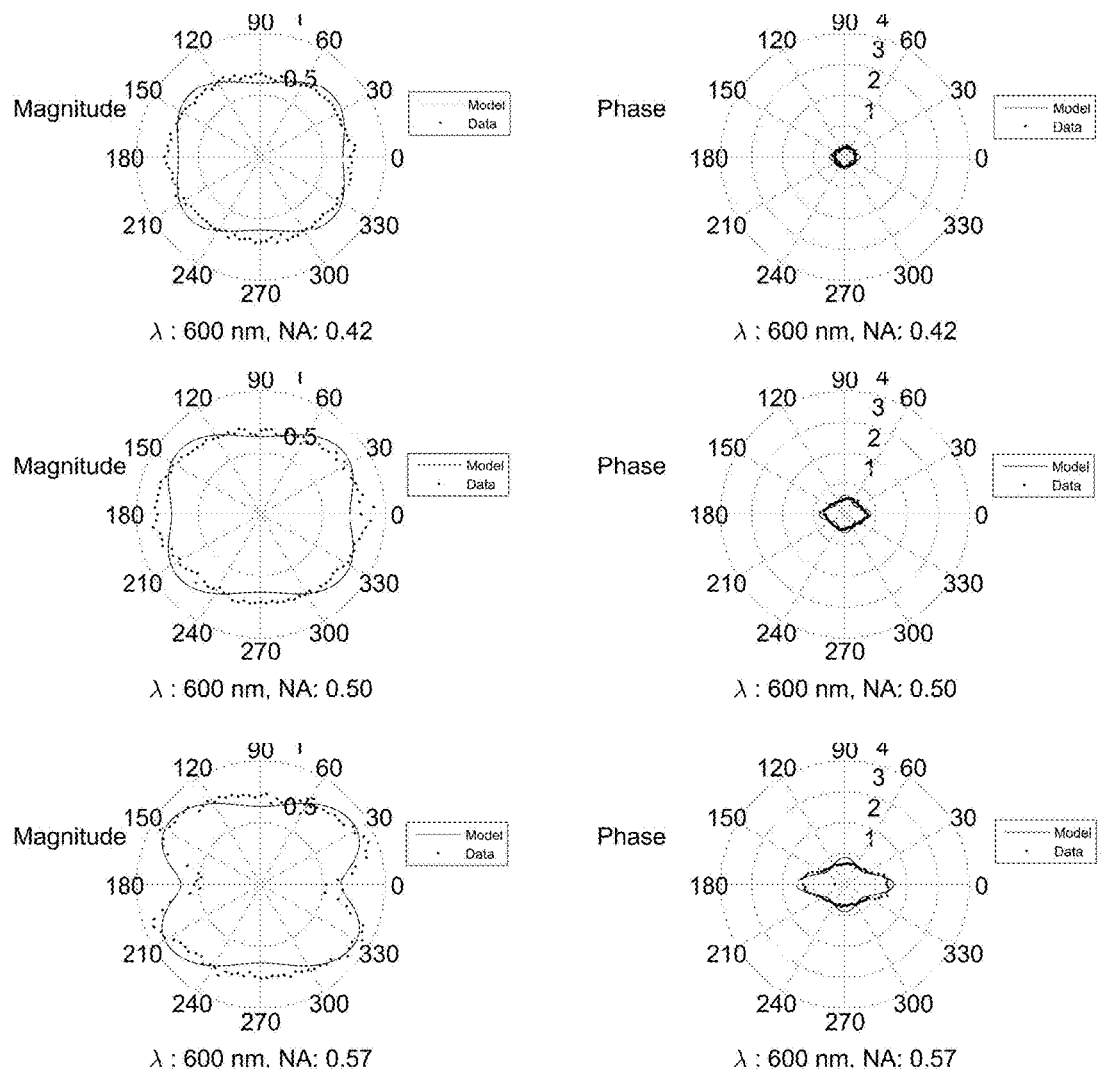

FIGS. 13A, 13B, and 13C are illustrations of the application of the described model to data collected on the optical metrology device 100 using a 5 µm spot size applied to a silicon dioxide grating with pitch of 360 nm, bottom critical dimension of 180 nm, and thickness of 300 nm on a (100) Si substrate for angle of incidence (numerical aperture) ranging from 24°-34° (0.41-0.57) at a wavelength of 540 nm. The continuous curves are the system model and the dotted curves are the experimental data.

As discussed above, in a pupil imaging system, such as that used by optical metrology device 100, the location of the center of the pupil of the aperture stop 108 is determined along with how to convert between a position on the detector and the angle of incidence (AOI) ($\phi$) and azimuth angle ($\theta$), e.g., in step 264 of FIG. 10. It is desirable to be able to measure the pupil plane at any time, rather than as a calibration step, and this all the more desirable when obtaining the pupil image involves moving an optical component, as done by the optical metrology device 100. While existing techniques may be used to determine the center of the pupil when the signal is obtained from a film sample, existing techniques do not work well when the signal is obtained from a patterned sample.

By way of example, if a pupil center of the optical metrology device 100 is to be found using a film sample, i.e., a flat reflective target, the Fourier transform signal F(X, Y, K) at position (X, Y) and spatial frequency K depends on: a) the source spectrum V(k) (k=2π/λ); b) the angle of incidence $\phi$, at which the spatial frequency K=2 k cos $\phi$; c) the reflectance of the sample r($\phi$, $\theta$, k) at angle of incidence $\phi$, azimuth angle $\theta$ and spatial frequency k; d) the relative (normalized) spatial variation of illumination in the pupil plane P(X, Y); e) the location of the pupil center ($X_0$, $Y_0$); and the scaling (A, B) between (X, Y) and angle of incidence $\phi$ as follows.

$$I(X, Y, K) = V\left(\frac{K}{2\cos\phi}\right) P(X, Y) r(\phi, \theta, k) \quad \text{(Eq. 15)}$$

$$\sin^2 \phi = A^2 (X-X_0)^2 + B^2 (Y-Y_0)^2 \quad \text{(Eq. 16)}$$

In the case of a thin-film or suitable single surface reflector such as chrome, the reflectance r($\phi$, $\theta$, k) varies very slowly, and so to a good approximation the spatial frequency, $K_{pk}$, at which S(X, Y, K) is a maximum may be written as follows.

$$K_{pk}(X,Y) = K_{pk}(X_0, Y_0) \cos \phi(X,Y) \quad \text{(Eq. 17)}$$

Combining (Eq. 16) and (Eq. 17) results in the following.

$$K_{pk}^2(X,Y) = K_{pk}^2(X_0, Y_0)(1-\sin^2 \phi) = K_{pk}^2(X_0, Y_0)(1-A^2(X-X_0)^2 - B^2(Y-Y_0)^2) \quad \text{(Eq. 18)}$$

So that $$K_{pk}^2(X,Y) = K_{pk}^2(X_0, Y_0)(1 - A^2 X^2 + 2A^2 X_0 X - A^2 X_0^2 - B^2 Y^2 + 2B^2 Y_0 Y - BY) \quad \text{(Eq. 19)}$$

If we fit measured values of $K_{pk}^2(X, Y)$ to a power series in pixel locations X and Y:

$$K_{pk}^2(X,Y) = C_0 + C_{x1} X + C_{x2} X^2 + C_{y1} Y + C_{y2} Y^2 \quad \text{(Eq. 20)}$$

The values $X_0$, $Y_0$, A, and B may be determined as follows:

$$X_0 = -\frac{C_{x1}}{2C_{x2}} \quad \text{(Eq. 21)}$$

$$Y_0 = -\frac{C_{y1}}{2C_{y2}} \quad \text{(Eq. 22)}$$

$$A = \sqrt{\frac{-C_{x2}}{C_0 - C_{x2} X_0^2 - C_{y2} Y_0^2}} \quad \text{(Eq. 23)}$$

$$B = \sqrt{\frac{-C_{y2}}{C_0 - C_{x2} X_0^2 - C_{y2} Y_0^2}} \quad \text{(Eq. 24)}$$

Figure 14:
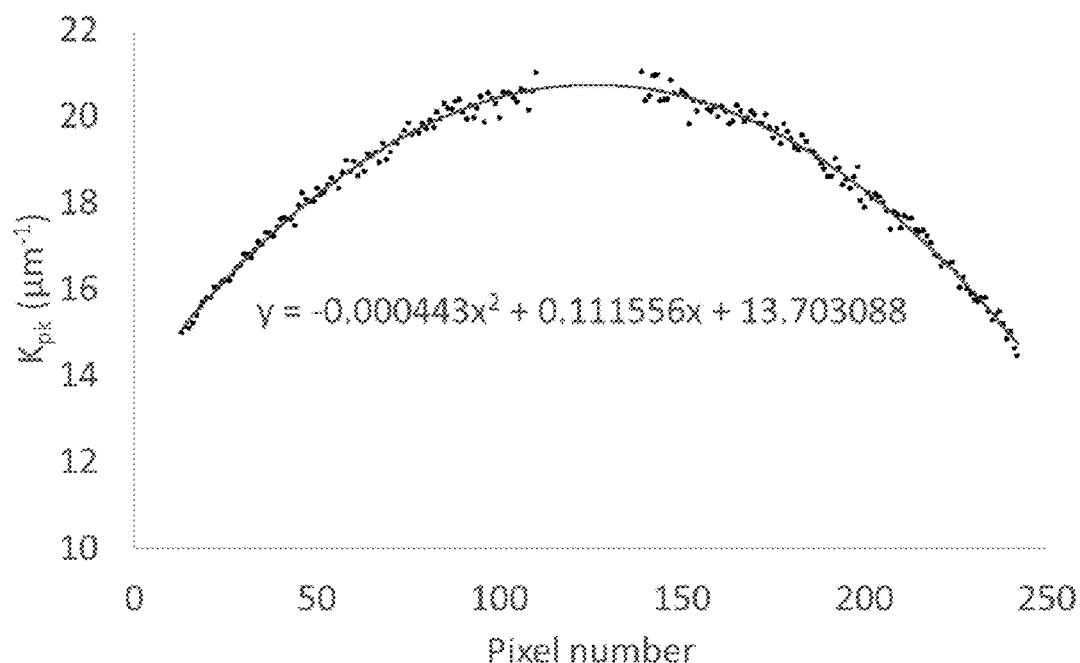
FIG. 14 illustrates a sample plot along the y axis only for $K_{pk}$ vs. pixel number with a quadratic fit measured using unpatterned sample.
Figure 15:
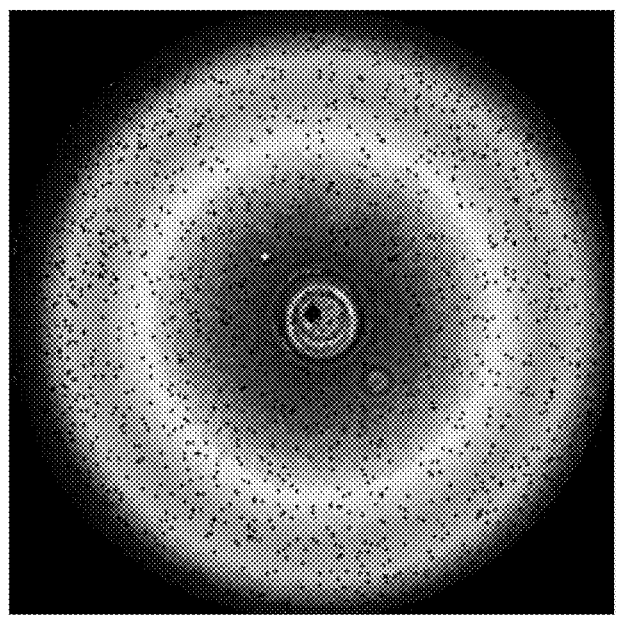
FIG. 15 illustrates a contour plot for $K_{pk}$ for all pixels within the pupil for the same sample used for FIG. 14.

FIG. 14, by way of example, illustrates a sample plot of a quadratic fit along the Y axis only for $K_{pk}$ vs. pixel number measured using a 27.1 nm thick layer of $SiO_2$ on silicon. The gap in the middle of the curve shown in FIG. 14 occurs in the region obscured by the reference mirror in the Mirau objective. The figure shows the best quadratic fit to the data. Using (Eq. 21)-(Eq. 24) gives $Y_0$=125.9 and A=0.0046, assuming Y=$Y_0$. FIG. 15 illustrates a contour plot for $K_{pk}$ for all pixels within the pupil for the same sample used for FIG. 14. The black spots in FIG. 15 arise at points where no calculation was done because of a weak signal.

For a well characterized thin film or single surface, where the materials thickness and optical properties are available, the Fresnel equations can be used to calculate the sample reflectance, r($\phi$, $\theta$, k,). If the illumination level across the pupil, P(X, Y), is known, then the source spectrum V(k) can be calculated.

There are several possible methods for determining P(X, Y), including but not limited to using the following if the measured scanning white light interferometer (SWLI) signal is I(X, Y, Z).

One method is to use the signal level where there are no interference fringes, such as occurs at a long distance from the plane of maximum interference between the sample and reference beams, which we have defined as Z=0. The source intensity is proportional to the signal at large Z (Eq. 25).

$$P(x, y) \propto \lim_{Z \to \infty} I(X, Y, Z) \quad \text{(Eq. 25)}$$

Another method is to fit the signal at each pixel (X, Y) to an empirical model, in which the signal I(X, Y, Z) is the sum of a slowly varying background, A(X, Y, Z), and an interference signal, cos(kZ+α) that has a slowly varying envelope, B(X, Y, Z) (Eq. 26). Then use P(X, Y)=A(X, Y, 0), where Z=0 is defined in the same way for all (X, Y), e.g. it is the plane of focus or scan mid-point.

$$I(X,Y,Z) = A(X,Y,Z) + B(X,Y,Z)\cos(kZ+\alpha) \quad \text{(Eq. 26)}$$

The source spectrum V(k) can be measured using a Fourier transformed signal F(X, Y, K) from a calibration sample with known reflectance, r($\phi$, $\theta$, k), and the measured pupil distribution, P(X, Y) by applying the relationship K=2 k cos $\phi$ and with the appropriate conversion functions $\phi$(X, Y) and $\theta$(X, Y) (Eq. 27).

$$V(k) = \frac{\iint \frac{F(X, Y, K)}{P(X, Y) r(\phi(X, Y), \theta(X, Y), k)} dX dY}{\iint dX dY} \quad \text{(Eq. 27)}$$

If a large enough area is used for this calculation, then the effect of variation in P(X, Y) averages out, and the approximation P(X, Y)≈1 may be used in (Eq. 27) as follows:

$$V(k) \approx \frac{\iint \frac{F(X, Y, K)}{r(\phi(X, Y), \theta(X, Y), k)} dXdY}{\iint dXdY} \quad \text{(Eq. 28)}$$

All of the above alternate methods of determining P(X, Y) and V(k) may be implemented by the optical metrology device 100. For a thin SiO2 film of known thickness on a silicon substrate, or for a solid metal samples, (Eq. 28) provides an adequate estimate of the source spectrum V(k). The estimate may be improved by averaging results from multiple samples. FIG. 3, by way of example, shows a measured spectrum, converted to a function of wavelength using k=2π/λ as derived by combining the measured spectra from chrome and 27.1 nm SiO2 on Si samples.

Figure 16:
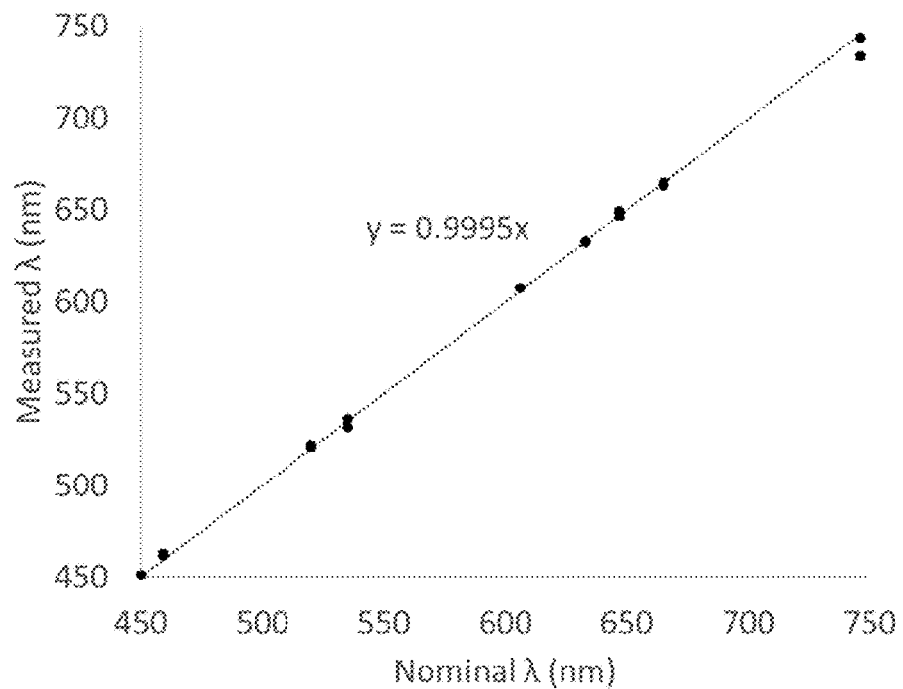
FIG. 16 illustrates a plot of the wavelength at the peak of each source spectrum I(k) with respect to the measured peak wavelength for several different narrow band filters in the illumination path of the scanning white-light interferometer.

Further validation of the method was performed by measuring V(k) with several different narrow-band (10 nm or 50 nm FWHM) filters in the illumination path after the aperture stop 108. FIG. 16, by way of example, illustrates the wavelength at the peak of each source spectrum V(k) plotted against the measured peak wavelength for each filter. For this test, (Eq. 28) was used in the calculation of the V(k) response. As can be seen, the agreement between the measured and expected peak wavelength is good, which provides justification for making the approximation P(X, Y)≈1 in (Eq. 27).

Figure 17A:
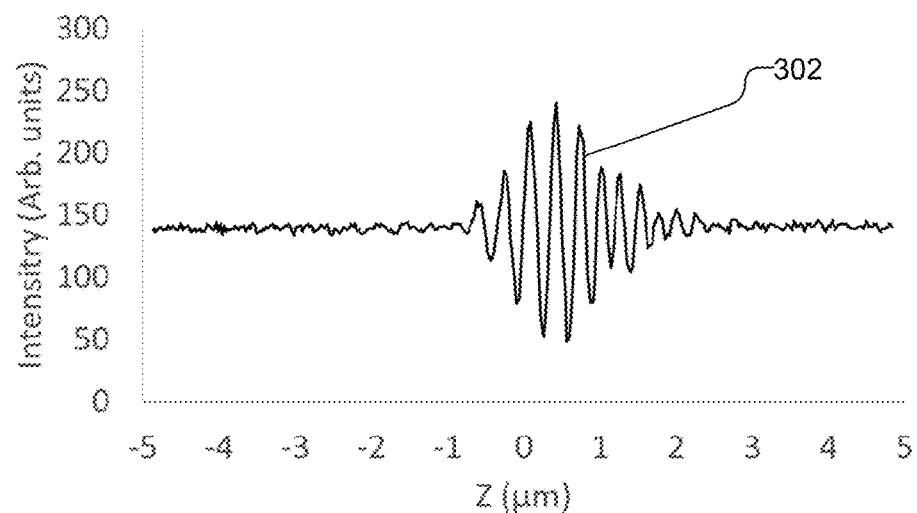
FIGS. 17A and 17B respectively illustrate a scanning white light interferometer signal and the signal Fourier Transform at one pixel in the pupil for an unpatterned sample.
Figure 17B:
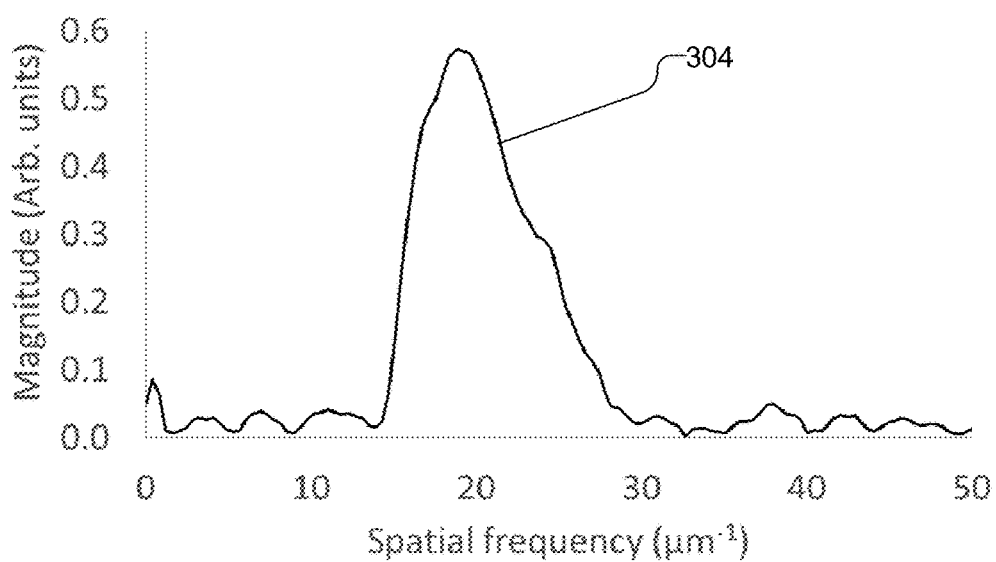

For films and simple surfaces, the Fourier transform signal F(X, Y, K) is closely related to the source spectrum V(k) because both the sample reflectance r(φ, θ, k) and the source spatial variation P(X, Y) change slowly or not at all with position and wavelength. FIGS. 17A and 17B, for example, respectively illustrate the scanning white light interferometer (SWLI) signal and the signal Fourier Transform at one pixel (X, Y) in the pupil for the 27.1 nm SiO2 on Si samples, where line 302 in FIG. 17A is the SWLI signal I(X, Y, Z), and in FIG. 17B line 304 is the amplitude of the signal Fourier Transform F(X, Y, K). With samples having gratings, however, there are locations with a fringe at some k, φ combinations, caused by the appearance or disappearance of non-zero diffraction orders according to the grating equation for grating pitch d and angle of incidence φ at zero azimuth angle θ:

$$d \sin \phi = n\lambda \quad \text{(Eq. 29)}$$

Figure 18:
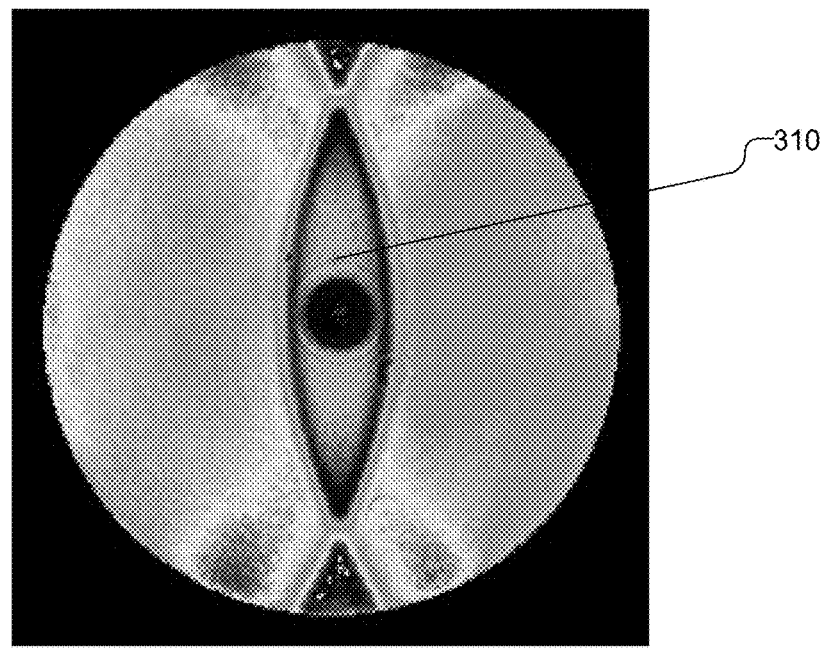
FIG. 18 illustrates a pupil plot showing the magnitude of the Fourier transform F(X, Y, k) for a grating sample.

FIG. 18 illustrates a pupil plot showing the magnitude of F(X, Y, k) for a SiO2 grating on Si having a 180 nm CD, 720 nm pitch, at for λ=632 nm, and illustrates an example of fringes caused by the appearance or disappearance of non-zero diffraction orders. The data in FIG. 18 has been interpolated to remove the angle of incidence dependence of the spatial frequency K, and hence is plotted for constant k=2π/λ.

Figure 19A:
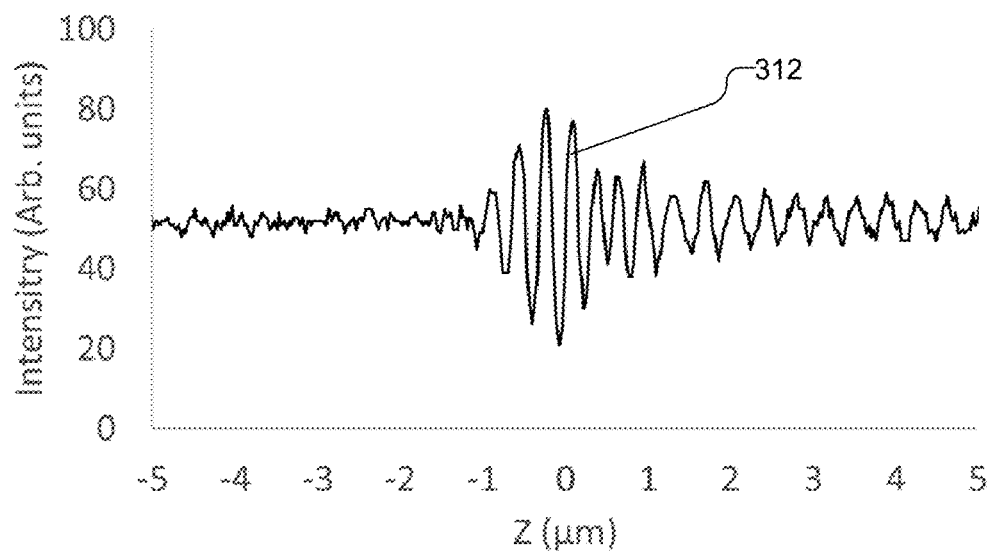
FIGS. 19A and 19B respectively illustrate the scanning white light interferometer signal and the signal Fourier Transform at the location marked by the small cross in FIG. 18.
Figure 19B:
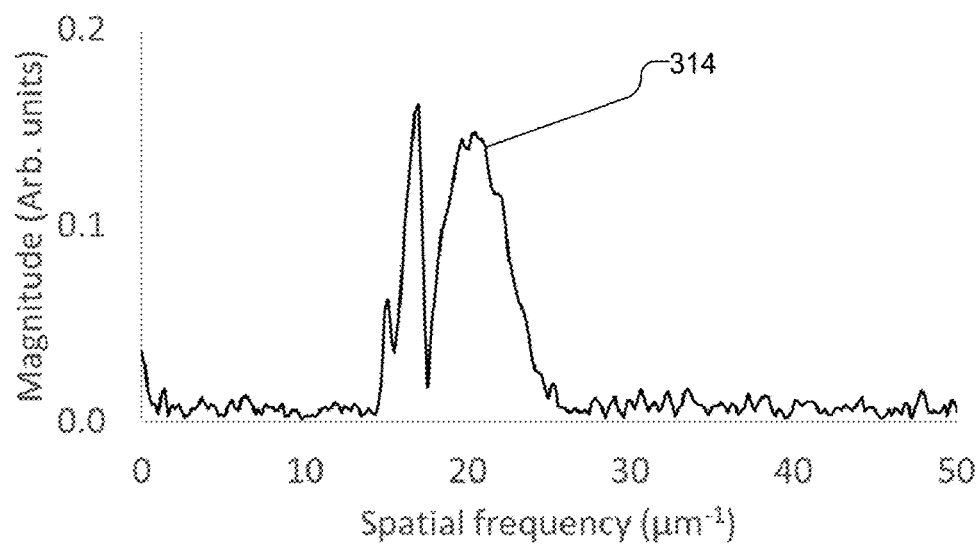

Since the fringe location depends on the wavelength, as per (Eq. 29), a fringe is not present for all values of K at a single (X, Y) position. FIGS. 19A and 19B respectively show the scanning white light interferometer (SWLI) signal and the signal Fourier Transform at the location marked by the small cross 310 in FIG. 18 for the 180 nm CD, 720 nm pitch SiO2 grating on Si, where line 312 in FIG. 19A is the SWLI signal I(X, Y, Z), and in FIG. 19B line 314 is the amplitude of signal Fourier Transform F(X, Y, K). The signal Fourier Transform F(X, Y, K) is a minimum near values of φ satisfying (Eq. 29). The method of finding the pupil center by fitting Kpk(X, Y) to a power series in x and y, as discussed in (Eq. 20)-(Eq. 24) fails when the sample has a grating, as Kpk can no longer be determined unambiguously.

When the sample to be measured includes a grating, the pupil center (X₀, Y₀) may be determined using calibration from a film target. Use of a calibration target, however, does not allow for movement of the pupil image between calibration and measurement due to variability in the position of moveable optical elements, such as the auxiliary lens 154. Alternatively, before each measurement of a patterned target, the moveable optical element, such as the auxiliary lens 154 may be positioned and the pupil center may be measured from a film area on the sample. Unfortunately, this process may be slow, especially if the auxiliary lens 154 must be switched before each measurement to allow pattern recognition to be used. Accordingly, it is desirable to be able to measure the pupil center $(X_0, Y_0)$ from a patterned sample.

Figure 20:
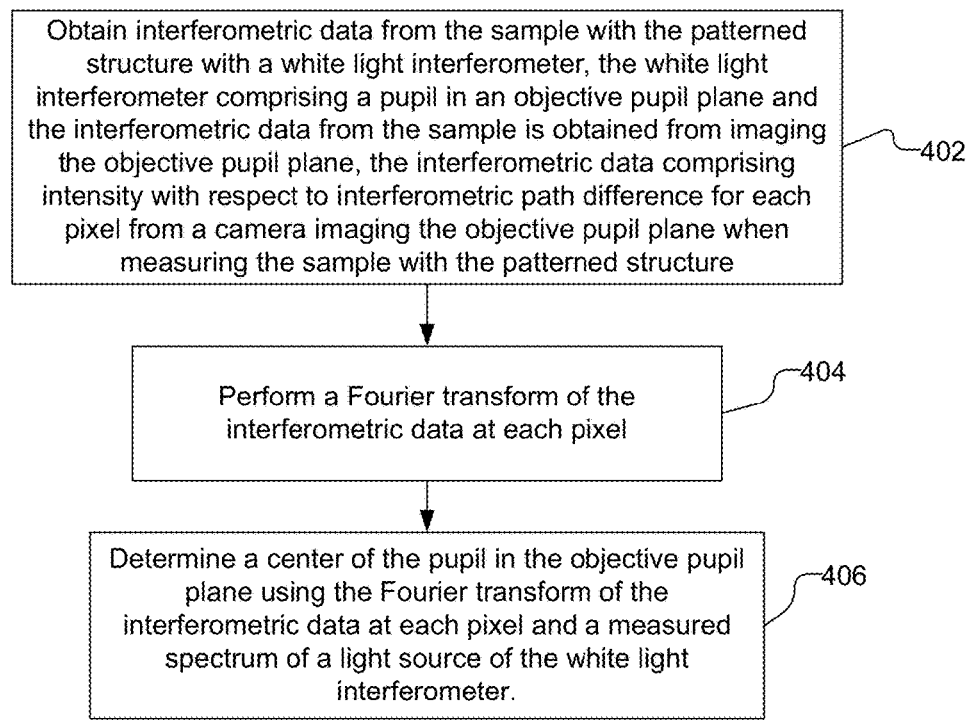
FIG. 20 is a flow chart illustrating a method of processing white light interferometric data from a sample with a patterned structure, and in particular determining the pupil center.

FIG. 20 shows a flow chart illustrating a method of processing white light interferometric data from a sample with a patterned structure, e.g., to determine the pupil center. As illustrated, interferometric data is obtained from the sample with the patterned structure with a white light interferometer (402), where the white light interferometer includes a pupil in an objective pupil plane and the interferometric data from the sample is obtained from imaging the objective pupil plane. The interferometric data comprises intensity with respect to optical path difference for each pixel from a camera imaging the objective pupil plane when measuring the sample with the patterned structure.

As discussed above, in FIG. 10, steps 252-258, the interferometric data may be obtained as an intensity signal with respect to the path difference z from the sample, and correcting the intensity signal with respect to z for variation in intensity at the pupil plane, e.g., using a measured intensity correction signal $C_1(X, Y)$ from a calibration sample as described previously.

A Fourier transform of the interferometric data is performed at each pixel (404). For example, as discussed at step 260 in FIG. 10, a Fourier transform may be applied to the corrected intensity signal at each pixel, to produce a Fourier signal F(X, Y, K), where K is a spatial frequency in the transform. If the data is generated by changing the z position by a constant amount from one image to the next, a Fast Fourier Transform may be used.

The center of the pupil, by way of example, may be determined by fitting the Fourier transform for each pixel to the measured spectrum of the light source to extract a scale factor linking the spatial frequency of the Fourier transform, K, to the spatial frequency of the source spectrum, V(k), through the relationship K=2 k cos φ. If the sample reflectance were constant, then the measured Fourier transform F(X, Y, K) is simply proportional to the frequency scaled source spectrum V(K/2 cos φ) (Eq. 30).

$$F(X,Y,Z) = F_0(X,Y) V(K/2 \cos \phi(X,Y)) \quad \text{(Eq. 30)}$$

The peak wavelength, for example, may be the wavelength that is the best fit. The center of the pupil may then be determined by extracting a characteristic wavelength, spatial frequency or equivalent description of the measured Fourier transform for each pixel by fitting the Fourier transform of the interferometric data at each pixel to the spectrum of the light source and fitting the characteristic wavelength, spatial frequency or equivalent description of the measured Fourier transform of every pixel to a calculated signal to find the center of the pupil in the objective pupil plane. For example, the peak wavelengths for every pixel may be fit to a quadratic power series.

Thus, to measure the pupil center $(X_0, Y_0)$ from a patterned sample, the measured signal Fourier Transform, $F(X, Y, K)$ is fitted to the spectrum $V(K/2 \cos \phi)$ obtained by analysis of data from a calibration sample, e.g., with a thin-film or chrome surface. The spectrum $V(k)$ is the measured spectrum which may be interpolated at arbitrary wavenumber k $(=2\pi/\lambda)$.

It may be desirable if $F_0(X, Y)$ is not floated in the model but is set initially, for example, using:

$$F_0(X, Y) = \frac{\max(F(X, Y, K))}{\max(V(k))} \quad \text{(Eq. 31)}$$

The actual fit is conveniently performed for $\cos \phi$ rather than $\phi$, using $D = \cos \phi$ in (Eq. 30) gives:

$$F(X,Y,K) = F_0(X,Y)V(K/2D(X,Y)) \quad \text{(Eq. 32)}$$

Thus, as can be seen, the process of fitting the Fourier transform of the interferometric data at each pixel to the measured spectrum of the light source yields best-fit values for the parameter $(F0(X, Y))$ and the cosine of an angle of incidence $(D(X, Y))$. Additionally, a weight may be determined based on the fit of the Fourier transform of the interferometric data at each pixel to the measured spectrum of the light source using Eq. 32. A weight $(W(X, Y))$ for the result, for example, is calculated as $(F_0(X, Y)/MSE)2$, where MSE is the sum for all K of the squares of the difference between the measured value $F(X, Y, K)$ and the best-fit model result $F_0(X, Y)V(K/2D(X, Y))$. The calculated values $D(X, Y)$ and $W(X, Y)$ will vary with pixel position $(X, Y)$. Since $D(X, Y)$ has been defined as the cosine of the angle of incidence $\phi(X, Y)$, $D(X, Y)$ must obey $-1 \leq D(X,Y) \leq +1$. The procedure must allow for values of $|D(X, Y)| > 1$ occurring due to signal noise, either by replacing values where $|D| > 1$ by sign(D) (+1 or −1), or by rejecting the data point.

The measured values of $D(X, Y)$ are fitted to a model for the variation of D with $(X, Y)$, Eq. 33, to produce best fit estimates for the pupil center location, $(X0, Y0)$ and the pixel to angle scale factors A and B.

$$D^2(X,Y) = 1 - \sin^2 \phi = 1 - A^2(X-X_0)^2 - B^2(Y-Y_0)^2 \quad \text{(Eq. 33)}$$

The weight $W(X, Y)$ is used to bias the fit by using values of $D(X, Y)$ with lower uncertainty. For example, the fit algorithm minimizes an indicator of how good the fit is, sometimes referred to as $\chi 2$. For example, if the a signal $y=f(X)$ is being fit to data $\{X_i, Y_i\}$, weights $W_i$ for each data point can be applied by using $\chi 2 = \Sigma(y_i - f(x_i))2 W_i / \Sigma W_i$.

In one implementation, the weight $W(X, Y)$ is determined from inverse of the mean square error of the best fit of the Fourier transform of the interferometric data at each pixel to the measured spectrum of the light source.

In another implementation, the weight is determined by dividing the fit constant $F_0(X, Y)$ by the mean square error of the best fit of the Fourier transform of the interferometric data at each pixel to the measured spectrum of the light source. Other methods of weighting the data will be apparent to those of ordinary skill in the art.

Figure 21:
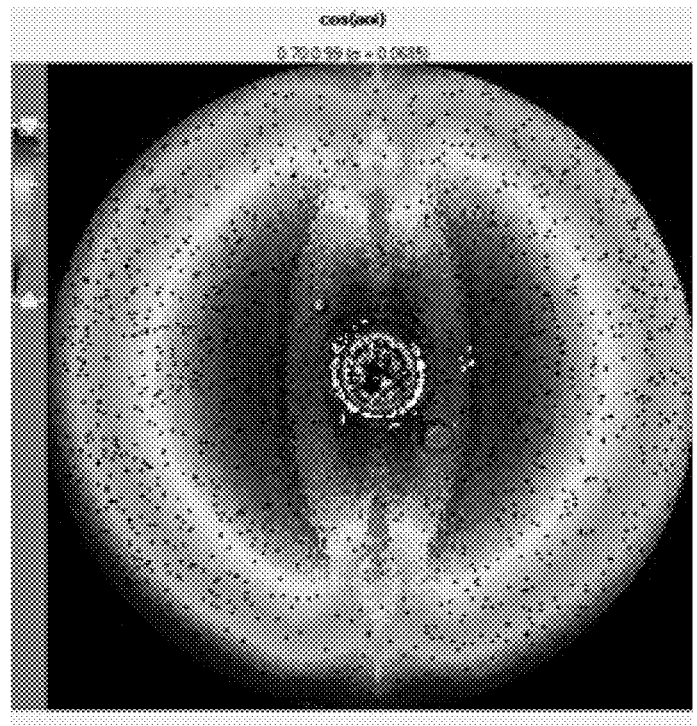
FIG. 21 illustrates the measured factors obtained by fitting the signal Fourier Transform F(X, Y, K) to a stored source spectrum I(k) for the grating sample used to generate FIG. 18.
Figure 22:
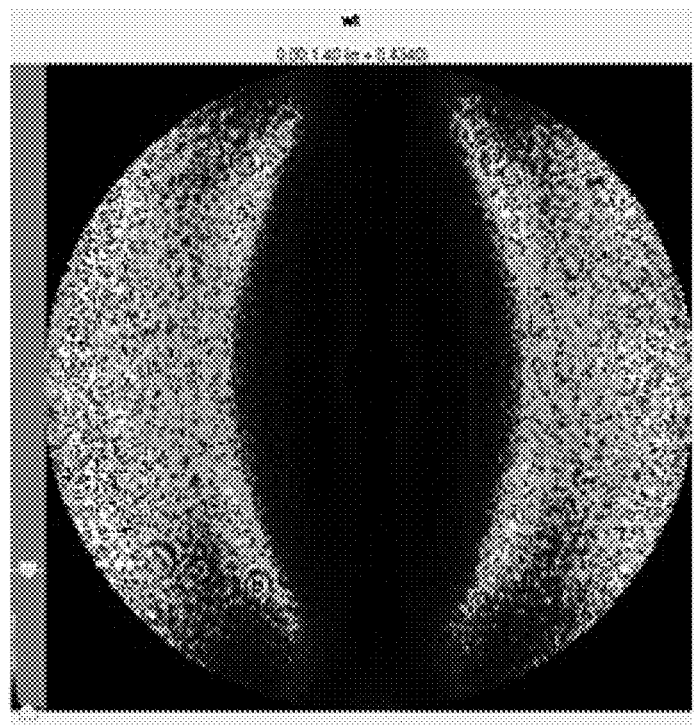
FIG. 22 shows the weighting calculated for the pupil center data shown in FIG. 21, where dark points indicate near-zero weight.

FIG. 21 illustrates the measured factors $1/D(X, Y)$ obtained by fitting the signal Fourier Transform $F(X, Y, K)$ to a stored source spectrum $I(k)$ for the same 180 nm CD 720 nm pitch SiO2 on Si grating used to generate FIG. 18. A comparison of FIG. 21 with FIG. 15 shows that the results are unreliable in the vicinity of the fringe pattern seen in FIG. 18. FIG. 22 shows the weight calculated for the pupil center data shown in FIG. 21, where dark points indicate near-zero weight. Data points for which a result $|D(X, Y)| > 1$ is calculated can be conveniently included by assigning them zero weight. As can be seen, points near the fringe pattern are given near zero weight, and so the calculation of the pupil center $(X_0, Y_0)$ using (Eq. 33) is improved, compared with the result obtained without weighting the data used in the fit. The measured pupil center position is $X_0=130.9$, $Y_0=133.1$.

Figure 23A:
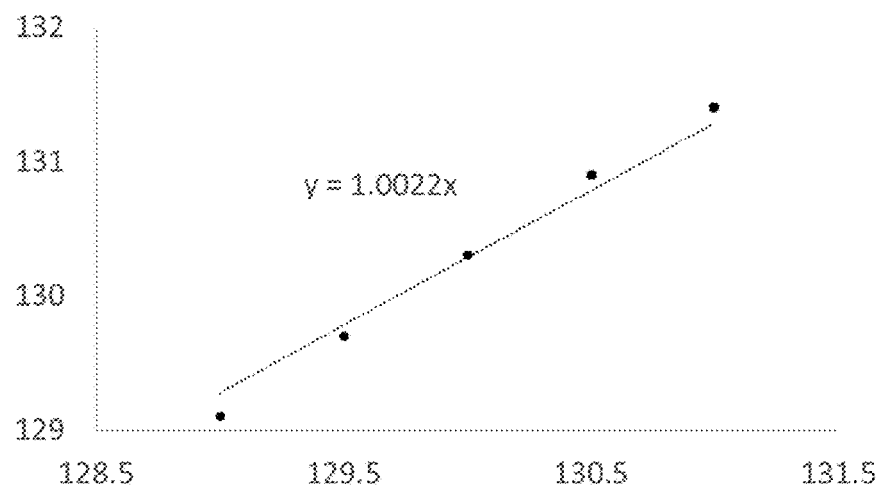
FIGS. 23A and 23B show comparisons between the fit results for the pupil along the X and Y axes, respectively, and manually derived results obtained by visually inspecting the pupil plane data.
Figure 23B:
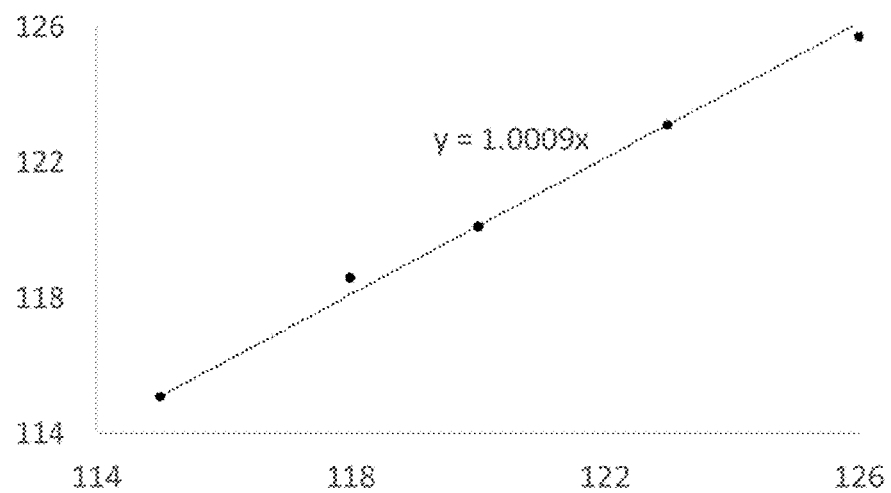

FIGS. 23A and 23B show comparisons between the fit results for the pupil center using (Eq. 32) along the X and Y axes, respectively, and manually derived results obtained by visually inspecting the pupil plane data. The sample used was the 180 nm CD 720 nm pitch grating used to create FIGS. 17 and 18 and the auxiliary lens 154 was moved so that the pupil center appeared at visibly different locations.

With the use of the pupil center determination process, an accurate measurement of the pupil center may be obtained from the measurement data, and thus, may be determined at the time of each new measurement. Accordingly, the requirement for prior calibration is reduced. Moreover, the process may be used with any sample, i.e., with a grating or unpatterned films. The process works with complex source spectra, for example, a multi-peaked source spectrum or if there are two or more maxima with similar intensity.

As discussed in FIG. 10, the method of processing the white light interferometric data may further include converting each pixel from the camera imaging the objective pupil plane into a unique set of angle of incidence and azimuth angle of light incident on the sample based on the center of the pupil in the objective pupil plane. Additionally, the center of the pupil may be provided to a sample model, and one or more characteristics of the sample are determined using the Fourier transform of the interferometric data at each pixel and the sample model.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method of characterizing a sample with a white light interferometer, the method comprising:

obtaining interferometric data from the sample with the white light interferometer, the interferometric data comprising intensity with respect to an optical path difference for each pixel from a camera imaging an objective pupil plane of the white light interferometer when measuring the sample;

extracting an electric field with complex parameters from the interferometric data, the electric field being a function of azimuth angle, angle of incidence and wavelength; and determining one or more characteristics of the sample using the electric field based on an electric field model of the azimuth angle, the angle of incidence and the wavelength that is specific for a zero diffraction order;

wherein extracting the electric field with complex parameters from the interferometric data comprises performing a Fourier transform of the interferometric data at each pixel, and wherein extracting the electric field comprises:

converting each pixel from the camera imaging the objective pupil plane into a unique set of angle of incidence and azimuth angle of light incident on the sample; and
converting each set of angle of incidence and spatial frequency from the Fourier transform to a wavelength;
wherein converting each pixel from the camera imaging the objective pupil plane into the unique set of angle of incidence and azimuth angle of the light incident on the sample comprises:
determining a center of a pupil in the objective pupil plane using the interferometric data from the sample; and
determining the unique set of angle of incidence and azimuth angle of the light incident on the sample for each pixel from the camera based on the center of the objective pupil in the objective pupil plane.

2. The method of claim 1, wherein the interferometric data from the sample does not include non-zero diffraction orders.

3. The method of claim 1, wherein determining the one or more characteristics of the sample using the electric field based on the electric field model of the azimuth angle, the angle of incidence and the wavelength comprises fitting the electric field extracted from the interferometric data to the electric field model.

4. The method of claim 3, wherein the electric field model includes contributions from a model sample, including one or more variable parameters, as well as from a model white light interferometer, including a diattenuation model for optical components of the white light interferometer and distribution in the objective pupil plane of intensity and phase of light from a light source for the white light interferometer.

5. The method of claim 1, wherein determining the one or more characteristics of the sample using the electric field based on the electric field model of the azimuth angle, the angle of incidence and the wavelength comprises using a library for the electric field model of the azimuth angle, the angle of incidence and the wavelength.

6. The method of claim 1, further comprising correcting the interferometric data for variation in intensity at the objective pupil plane.

7. The method of claim 6, wherein correcting the interferometric data for variation in intensity at the objective pupil plane comprises:
obtaining intensity correction data from a calibration sample, the intensity correction data comprising an intensity with respect to the optical path difference for each pixel from the camera imaging the objective pupil plane of the white light interferometer when measuring the calibration sample; and
adjusting the intensity with respect to the optical path difference for each pixel from the camera using the intensity correction data for each respective pixel from the camera.

8. The method of claim 6, wherein correcting the interferometric data for variation in intensity at the objective pupil plane comprises:
obtaining intensity correction data from a calibration sample, the intensity correction data comprising an intensity with spatial frequency for each pixel from the camera imaging the objective pupil plane of the white light interferometer when measuring the calibration sample;
performing a Fourier transform of the interferometric data at each pixel to produce a Fourier transformed signal; and
adjusting the Fourier transformed signal using the intensity correction data.

9. The method of claim 6, wherein correcting the interferometric data for variation in intensity at the objective pupil plane comprises:
obtaining intensity correction data from a calibration sample, the intensity correction data comprising an intensity with spatial frequency with respect to an angle of incidence and azimuth angle determined for each pixel from the camera imaging the objective pupil plane of the white light interferometer when measuring the calibration sample; and
performing a Fourier transform of the interferometric data at each pixel to produce a Fourier transformed signal;
converting each pixel for the Fourier transformed signal to the angle of incidence and azimuth angle; and
adjusting the Fourier transformed signal using the intensity correction data.

10. The method of claim 1, wherein determining the center of the pupil in the objective pupil plane using the interferometric data from the sample comprises:
extracting a scale factor for the wavelength or spatial frequency of the Fourier transform for each pixel by fitting the Fourier transform of the interferometric data at each pixel to a measured spectrum of the light source;
multiplying the wavelength or spatial frequency of the measured spectrum of the light source by the scale factor for every pixel; and
fitting the wavelength or spatial frequency of the measured spectrum multiplied by the scale factor for every pixel to a cosine function to find the center of the pupil in the objective pupil plane and a rate of change of the angle of incidence with distance in pixels from the pupil center.

11. The method of claim 10, wherein fitting the wavelength or spatial frequency of the measured spectrum multiplied by the scale factor for every pixel to the cosine function to find the center of the pupil in the objective pupil plane comprises weighting the wavelength or spatial frequency of the measured spectrum by a quality of fit to the measured spectrum of the light source.

12. The method of claim 1, wherein the electric field model is represented as a generalized Jones matrix.

13. The method of claim 1, wherein extracting the electric field comprises converting each pixel from the camera imaging the objective pupil plane into a unique set of angle of incidence and azimuth angle of light incident on the sample.

14. The method of claim 1, wherein obtaining interferometric data from the sample with the white light interferometer comprises using an output polarizer before the camera in the white light interferometer to suppress effects of undesired depolarization caused by optical elements in the white light interferometer.

15. The method of claim 1, wherein obtaining interferometric data from the sample with the white light interferometer comprises:
generating an illumination beam of broadband light;
using a beam splitter to direct the illumination beam through an aperture stop at the objective pupil plane;
polarizing the illumination beam;
using an interferometric objective lens to cause the illumination beam to be incident on the sample, wherein the illumination beam is reflected off the sample to produce a reflected beam;

receiving the reflected beam with the interferometric objective lens to direct the reflected beam towards the beam splitter;

polarizing the reflected beam;

using the beam splitter to direct the reflected beam towards the camera;

focusing an image of the objective pupil plane on the camera;

polarizing the reflected beam after the beam splitter directs the reflected beam towards the camera and before the reflected beam is received as the image of the objective pupil plane by the camera;

wherein the camera captures images of the objective pupil plane while the interferometric objective lens varies the optical path difference.

16. The method of claim 15, further comprising selectively focusing an image of the objective pupil plane on the camera or an image of the sample on the camera and capturing images of the sample with the camera.

17. The method of claim 15, further comprising diffusing the illumination beam prior to the illumination beam passing through the aperture stop at the objective pupil plane to reduce variation in intensity at the objective pupil plane.

18. The method of claim 1, wherein obtaining the interferometric data comprises polarizing an illumination beam and prior to a detection system using a polarizing beam splitter cube to send light with a first polarization to the camera and light with a different polarization to a different camera.

19. A white light interferometer capable of characterizing a sample, the white light interferometer comprising:

a broadband light source that produces an illumination beam of broadband light;

a beam splitter that directs the illumination beam toward the sample and directs the illumination beam through an aperture stop at an objective pupil plane, wherein the illumination beam is reflected by the sample to form a reflected beam, the beam splitter directs the reflected beam towards a camera;

an interferometric objective lens that receives the illumination beam and focuses the illumination beam on the sample, the interferometric objective lens comprising a reference mirror to form a reference beam, wherein the reflected beam combines with the reference beam to produce interference in the reflected beam based on an optical path difference between the reflected beam and the reference beam;

the camera having a plurality of pixels, the camera captures images of the objective pupil plane while the optical path difference is varied to produce interferometric data for the sample, the interferometric data comprising intensity with respect to the optical path difference at each pixel; and at least one processor coupled to receive the interferometric data for the sample, the at least one processor extracts an electric field with complex parameters from the interferometric data, the electric field being a function of azimuth angle, angle of incidence and wavelength, and determines one or more characteristics of the sample using the electric field based on an electric field model of the azimuth angle, the angle of incidence and the wavelength that is specific for a zero diffraction order;

wherein the at least one processor performs a Fourier transform of the interferometric data at each pixel to extract the electric field with complex parameters from the interferometric data;

wherein the at least one processor converts each pixel from the camera imaging the objective pupil plane into a unique set of angle of incidence and azimuth angle of light incident on the sample, and converts each set of angle of incidence and spatial frequency from the Fourier transform to a wavelength to extract the electric field with complex parameters from the interferometric data;

wherein the at least one processor determines a center of a pupil in the objective pupil plane using the interferometric data from the sample, and determines the unique set of angle of incidence and azimuth angle of the light incident on the sample for each pixel from the camera based on the center of the objective pupil in the objective pupil plane to convert each pixel from the camera imaging the objective pupil plane into the unique set of angle of incidence and azimuth angle of the light incident on the sample.

20. The white light interferometer of claim 19, wherein the interferometric data from the sample does not include non-zero diffraction orders.

21. The white light interferometer of claim 19, wherein the at least one processor fits the electric field extracted from the interferometric data to the electric field model to determine the one or more characteristics of the sample using the electric field based on the electric field model of the azimuth angle, the angle of incidence and the wavelength.

22. The white light interferometer of claim 21, wherein the electric field model includes contributions from a model sample, including one or more variable parameters, as well as from a model white light interferometer, including a diattenuation model for optical components of the white light interferometer and distribution in the objective pupil plane of intensity and phase of light from the broadband light source of the white light interferometer.

23. The white light interferometer of claim 19, wherein the at least one processor uses a library for the electric field model of the azimuth angle, the angle of incidence and the wavelength to determine the one or more characteristics of the sample using the electric field based on the electric field model of the azimuth angle, the angle of incidence and the wavelength.

24. The white light interferometer of claim 19, wherein the at least one processor corrects the interferometric data for variation in intensity at the objective pupil plane.

25. The white light interferometer of claim 24, wherein the at least one processor obtains intensity correction data from a calibration sample, the intensity correction data comprising an intensity with respect to the optical path difference for each pixel from the camera imaging the objective pupil plane of the white light interferometer when measuring the calibration sample, and adjusts the intensity with respect to the optical path difference for each pixel from the camera using the intensity correction data for each respective pixel from the camera to correct the interferometric data for variation in intensity at the objective pupil plane.

26. The white light interferometer of claim 24, wherein the at least one processor obtains intensity correction data from a calibration sample, the intensity correction data comprising an intensity with spatial frequency for each pixel from the camera imaging the objective pupil plane of the white light interferometer when measuring the calibration sample, performs a Fourier transform of the interferometric data at each pixel to produce a Fourier transformed signal, and adjusts the Fourier transformed signal using the intensity correction data to correct the interferometric data for variation in intensity at the objective pupil plane.

27. The white light interferometer of claim 24, wherein obtains intensity correction data from a calibration sample, the intensity correction data comprising an intensity with spatial frequency with respect to an angle of incidence and azimuth angle determined for each pixel from the camera imaging the objective pupil plane of the white light interferometer when measuring the calibration sample; performs a Fourier transform of the interferometric data at each pixel to produce a Fourier transformed signal, converts each pixel for the Fourier transformed signal to the angle of incidence and azimuth angle, and adjusts the Fourier transformed signal using the intensity correction data to correct the interferometric data for variation in intensity at the objective pupil plane.

28. The white light interferometer of claim 19, the at least one processor extracts a scale factor for the wavelength or spatial frequency of the Fourier transform for each pixel by fitting the Fourier transform of the interferometric data at each pixel to a measured spectrum of the light source, multiplies the wavelength or spatial frequency of the measured spectrum of the light source by the scale factor for every pixel, and fits the wavelength or spatial frequency of the measured spectrum multiplied by the scale factor for every pixel to a cosine function to find the center of the pupil in the objective pupil plane and a rate of change of the angle of incidence with distance in pixels from the pupil center to determine the center of the pupil in the objective pupil plane using the interferometric data from the sample.

29. The white light interferometer of claim 28, wherein the at least one processor weights the wavelength or spatial frequency of the measured spectrum by a quality of fit to the measured spectrum of the light source to fit the wavelength or spatial frequency of the measured spectrum multiplied by the scale factor for every pixel to the cosine function.

30. The white light interferometer of claim 19, wherein the electric field model is represented as a generalized Jones matrix.

31. The white light interferometer of claim 19, wherein the at least one processor converts each pixel from the camera imaging the objective pupil plane into a unique set of angle of incidence and azimuth angle of light incident on the sample to extract the electric field.

32. The white light interferometer of claim 19, further comprising a polarizer positioned before the camera, the polarizer suppresses effects of undesired depolarization caused by at least one of the optical system, the beam splitter, and the interferometric objective lens.

33. The white light interferometer of claim 19, further comprising:
  an optical system that receives the reflected beam from the beam splitter, the optical system being configurable to selectively focus an image of the objective pupil plane on the camera and an image of the sample on the camera;
  wherein the camera further captures images of the sample.

34. The white light interferometer of claim 19, further comprising a diffuser positioned prior to the aperture stop at the objective pupil plane, the diffuser diffuses the illumination beam passing through the aperture stop at the objective pupil plane to reduce variation in intensity at the objective pupil plane.

35. The white light interferometer of claim 19, further comprising:
  a first polarizer that polarizes the illumination beam; and
  a polarizing beam splitter cube that sends light from the reflected beam having a first polarization to the camera and sends light from the reflected beam having a different polarization to a second camera.

* * * * *